(12) United States Patent
Mackenzie et al.

(10) Patent No.: US 7,056,996 B2
(45) Date of Patent: Jun. 6, 2006

(54) PRODUCTIVITY CATALYSTS AND MICROSTRUCTURE CONTROL

(75) Inventors: Peter Borden Mackenzie, Kingsport, TN (US); Leslie Shane Moody, Johnson City, TN (US); James Allen Ponasik, Jr., Blountville, TN (US); Amy Kathryn Farthing, Gray, TN (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 110 days.

(21) Appl. No.: 10/648,357

(22) Filed: Aug. 27, 2003

(65) Prior Publication Data

US 2004/0077809 A1 Apr. 22, 2004

Related U.S. Application Data

(63) Continuation-in-part of application No. 09/985,614, filed on Nov. 5, 2001, which is a continuation-in-part of application No. 09/563,812, filed on May 3, 2000, now Pat. No. 6,545,108, which is a continuation-in-part of application No. 09/507,492, filed on Feb. 18, 2000, now Pat. No. 6,559,091.

(60) Provisional application No. 60/298,893, filed on Jun. 19, 2001, provisional application No. 60/246,254, filed on Nov. 6, 2000, provisional application No. 60/246,255, filed on Nov. 6, 2000, provisional application No. 60/246,178, filed on Nov. 6, 2000, provisional application No. 60/231,920, filed on Sep. 11, 2000.

(51) Int. Cl.
*C08F 4/44* (2006.01)
*B01J 31/00* (2006.01)

(52) U.S. Cl. .................. 526/161; 526/172; 502/167

(58) Field of Classification Search ................ 502/167; 526/132, 134, 161, 172
See application file for complete search history.

(56) References Cited

U.S. PATENT DOCUMENTS

| | | | |
|---|---|---|---|
| 4,564,647 A | 1/1986 | Hayashi et al. | |
| 4,724,273 A | 2/1988 | Fink et al. | |
| 4,752,597 A | 6/1988 | Turner | |
| 5,106,804 A | 4/1992 | Bailly et al. | |
| 5,132,380 A | 7/1992 | Stevens et al. | |
| 5,227,440 A | 7/1993 | Canich et al. | |
| 5,296,565 A | 3/1994 | Ueda et al. | |
| 5,324,800 A | 6/1994 | Welborn, Jr. et al. | |
| 5,331,071 A | 7/1994 | Kataoka et al. | |
| 5,332,706 A | 7/1994 | Nowlin et al. | |
| 5,350,723 A | 9/1994 | Neithamer et al. | |
| 5,399,635 A | 3/1995 | Neithamer et al. | |
| 5,466,766 A | 11/1995 | Patsidis et al. | |
| 5,468,702 A | 11/1995 | Jejelowo | |
| 5,474,962 A | 12/1995 | Takahashi et al. | |
| 5,578,537 A | 11/1996 | Herrmann et al. | |
| 5,863,853 A | 1/1999 | Vaughan et al. | |
| 5,866,663 A | 2/1999 | Brookhart et al. | |
| 5,880,241 A | 3/1999 | Brookhart et al. | |
| 5,880,323 A | 3/1999 | Brookhart, III et al. | |
| 5,886,224 A | 3/1999 | Brookhart et al. | |
| 5,891,963 A | 4/1999 | Brookhart et al. | |
| 6,197,715 B1 | 3/2001 | Bansleben et al. | |
| 6,559,091 B1 * | 5/2003 | Moody et al. | ............ 502/167 |

FOREIGN PATENT DOCUMENTS

| | | |
|---|---|---|
| DE | 19707236 A1 | 8/1998 |
| DE | 19959251 A1 | 12/1999 |
| DE | 19944993 A1 | 3/2001 |
| EP | 0 381 495 A2 | 8/1990 |
| EP | 0 416 815 A2 | 3/1991 |
| EP | 0 420 436 A1 | 4/1991 |
| EP | 0 532 098 A1 | 3/1993 |
| EP | 0 641 804 A2 | 3/1995 |
| EP | 0 816 384 A2 | 1/1998 |
| EP | 0 874 005 A1 | 10/1998 |
| EP | 0 884 331 A2 | 12/1998 |
| EP | 0 893 455 A1 | 1/1999 |
| EP | 1 099 714 A1 | 11/1999 |
| JP | 10-324709 | 3/1997 |
| JP | HEI 9-255712 | 9/1997 |
| JP | HEI 9-272709 | 10/1997 |
| JP | HEI 9-272713 | 10/1997 |
| WO | 94/01471 | 1/1994 |
| WO | 94/11410 | 5/1994 |
| WO | 94/14854 | 7/1994 |
| WO | 96/23010 | 8/1996 |
| WO | 97/02298 | 1/1997 |
| WO | 97/17380 | 5/1997 |
| WO | 97/38024 | 10/1997 |
| WO | 97/48735 | 12/1997 |
| WO | 97/48736 | 12/1997 |

(Continued)

OTHER PUBLICATIONS

A. Bach, et al., "Metal Chelates of N-(1-Pyrrolyl)salicylaldimines and Their Structure Determination by X-Ray Structure Analysis and X-Ray Absorption Spectroscopy (XANES)," *Z. Naturforsch., Chem. Sci.*, 1996, pp. 757-764, vol. 51(6).

(Continued)

*Primary Examiner*—Robert D. Harlan

(57) ABSTRACT

Improved Group 3–11 transition metal based catalysts and processes for the polymerization of olefins are described. Some of the ligands are characterized by a preferred substitution pattern which allows for higher productivities of highly branched olefins; substitution patterns which boost productivity or alter the polymer microstructure are also described.

22 Claims, No Drawings

FOREIGN PATENT DOCUMENTS

| | | |
|---|---|---|
| WO | 97/48737 | 12/1997 |
| WO | 97/48739 | 12/1997 |
| WO | 97/48740 | 12/1997 |
| WO | 97/48742 | 12/1997 |
| WO | 97/48777 | 12/1997 |
| WO | 98/03521 A | 1/1998 |
| WO | 98/03559 | 1/1998 |
| WO | 98/11144 | 3/1998 |
| WO | 98/27124 | 6/1998 |
| WO | 98/30609 | 7/1998 |
| WO | 98/30610 | 7/1998 |
| WO | 98/37110 | 8/1998 |
| WO | 98/40374 | 9/1998 |
| WO | 98/40420 | 9/1998 |
| WO | 98/40421 | 9/1998 |
| WO | 98/41529 | 9/1998 |
| WO | 98/42664 | 10/1998 |
| WO | 98/42665 | 10/1998 |
| WO | 98/47933 | 10/1998 |
| WO | 98/47934 | 10/1998 |
| WO | 98/56832 | 12/1998 |
| WO | 99/02472 | 1/1999 |
| WO | 99/02570 | 1/1999 |
| WO | 00/47592 A1 | 2/1999 |
| WO | 99/05189 | 2/1999 |
| WO | 99/09078 | 2/1999 |
| WO | 00/58320 A1 | 3/1999 |
| WO | 99/10391 | 3/1999 |
| WO | 99/12981 | 3/1999 |
| WO | 01/07491 A1 | 7/1999 |
| WO | 01/12684 A1 | 8/1999 |
| WO | 01/07492 A1 | 9/1999 |
| WO | 01/14391 A1 | 9/1999 |
| WO | 01/21586 A1 | 9/1999 |
| WO | 01/23396 A1 | 9/1999 |
| WO | 01/42257 A1 | 12/1999 |
| WO | 99/62968 A | 12/1999 |
| WO | 00/04057 | 1/2000 |
| WO | 01/55231 A1 | 1/2000 |
| WO | 00 15646 A | 3/2000 |
| WO | 00/50470 A | 8/2000 |
| WO | 01/92342 A | 12/2001 |

OTHER PUBLICATIONS

A. V. Bordunov, et al., "Azacrown Ethers Containing Oximic and Schiff Base Sidearms—Potential Heteronuclear Metal Ion Receptors," *Tetrahedron, NL,* Dec. 29, 1997, pp. 17595-17606, vol. 53, No. 52, Elsevier Science Publishers, Amsterdam.

M. Brookhart et al., *J. Am. Chem. Soc.*, 1995, pp. 6414-6415, 117.

Buelow, "Chemische Berichte," *Berichte Der Deutschen Chemischen Gesellschaft, DE, Verlag Chemie. Weinheim,* 1905, pp. 3915, 3917, vol. 38.

R. M. Claramunt, et al., "Rhodium (I) Complexes with the Polydentate Ligand 3,5-bis(4-methylpyrazol-1-yl)-4-methylpyrazole," *Journal Organometallic Chemistry,* 1991, pp. 259-271, vol. 412, No. 1-2.

I. O. Fritsky, et al., "Template Synthesis of Square-Planar Nickel (II) and Copper (III) Complexes Based on Hydrazide Ligands," *J. Chem. Soc., Dalton Trans.,* 1998, pp. 3269-3274, vol. 19.

V. C. Gibson et al., *Chem. Commun.,* 1998, pp. 313-314.

S. D. Ittel et al., "Late-Metal Catalysts for Ethylene Homo- and Copolymerization," *Chem. Rev.,* 2000, pp. 1169-1203, 100.

W. Keim et al., *Angew Chem. Int. Ed. Engl.,* 1981, pp. 116-117, 20.

D. H. McConville et al., *J. Am. Chem. Soc.,* 1996, pp. 10008-10009, 118.

Oleg V. Mikhailov, "From Novel Complexing Conditions to Novel Coordination Compounds of Nickel (II) with Dithiooxamide and its Bulky Analogues," *Transition Met. Chem.,* (1996), 363-369, 21.

V. M. Mohring et al., *Agnew. Chem. Int. Ed. Engl.,* 1985, pp. 1001-1003, 24.

K. K. Narang, et al., Glyoxal-Aroyl Hydrazone (Schiff Base) Complexes of Nickel (II), Copper (II) & Zinc (II), *Indian J. Chem., Sect. A.,* 1982, pp. 830-832, vol. 21A(8).

K. K. Narang, et al., "Synthesis, Characterization, Thermal Studies and Biological Activity of Iron (III) Complexes with Some Acylhydrazines," *Synth. React. Inorg. Met.-Org. Chem.,* 1993, pp. 971-989, vol. 23(6).

F. A. Neugebauer, "ESR Studies of 1,2,4,5-Tetraazapentenyls," *Chem. Ber.,* 1973, pp. 1716-1723, vol. 106(6).

M. Peuckert et al., *Organometallics,* 1983, pp. 594-597, 2.

Timo Repo, et al., "Ethylenebis(Salicylidenetiminato)zirconium Dichloride: Crystal Structure and Use as a Heterogeneous Catalyst in the Polymerization of Ethylene," *Maromolecules,* (1997), 171-175, 30.

S. B. Roscoe et al., "Polyolefin Spheres from Metallocenes Supported on Noninteracting Polystyrene," *Science,* 1998, pp. 270-273, 280.

L. Rosenberg, et al., "Binuclear Nickel (II) and Cobalt (II) Complexes of the Novel Binucleating Ligand 3,-Bis(1'-pyrazolyl)pyridazine. Crystal and Molecular Structure and Magnetism of Bis[μ-3,6-bis(1'-pyrazolyl)pyridazine-$N^1(Ni^1)N^{2+}(Ni^1)N^{2+}(Ni^1)N^2(Ni^2)N^{2''}(Ni^{21})$]-bis[diaquanickel (II)] Tetrachloride Dihydrate," *J. Chem. Soc., Dalon Trans.,* 1986, pp. 625-631, vol. 3.

M. Schmid et al., "New $C_2$/ and Chiral $C_2$-Symmetric Olefin Polymerization Catalysts Based on Nickel (II) and Palladium (II) Diimine Complexes Bearing 2,6-Diphenyl Aniline Moieties: Synthesis, Structural Characterization, and First Insight into Polymerization Properties," *Organometallics,* 2001, 20(11), 2321.

R. R. Schrock et al., *J. Am. Chem. Soc.,* 1997, pp. 3830-3831, 119.

R. R. Schrock et al., *J. Am. Chem. Soc.,* 1999, pp. 5797-5798, 121.

S. H. Strauss, *Chem. Rev.,* 1993, pp. 927-942, 93.

A. A. Watson, et al., "Chiral Heterocyclic Ligands. VIII. Syntheses and Complexes of New Chelating Ligands Derived from Camphor," *Aust. J. Chem.,* 1995, pp. 1549-1572, vol. 48, No. 9.

\* cited by examiner

PRODUCTIVITY CATALYSTS AND MICROSTRUCTURE CONTROL

CROSS REFERENCE TO RELATED APPLICATIONS

This is a continuation-in-part of application Ser. No. 09/985,614, filed Nov. 5, 2001; which is a continuation-in-part of application Ser. No. 09/563,812, filed May 3, 2000 now U.S. Pat. No. 6,545,108; which is a continuation-in-part of application Ser. No. 09/507,492, filed Feb. 18, 2000 now U.S. Pat. No. 6,559,091, the entire contents of which are incorporated herein by reference. The '614 application claims the benefit of the following applications under 35 USC § 119: Provisional Application No. 60/231,920, filed Sep. 11, 2000; Provisional Application No. 60/246,254, filed Nov. 6, 2000; Provisional Application No. 60/246,255, filed Nov. 6, 2000; Provisional Application No. 60/246,178, filed Nov. 6, 2000; and Provisional Application No. 60/298,893, filed Jun. 19, 2001, the entire contents of which are incorporated herein by reference.

FIELD OF THE INVENTION

This application generally relates to olefin polymerization catalyst compositions and olefin polymerization processes using the same, and to new polyolefin compositions.

BACKGROUND OF THE INVENTION

The use of late transition metal complexes as catalysts for olefin polymerization has recently been reviewed by Ittel et al. (*Chem. Rev.* 2000, 100, 1169). Notwithstanding the many advances described therein, there remains a need for new late transition metal catalysts with improved productivities under commercial reactor operating conditions, and for new methods of microstructure control. Late transition metal catalysts and processes that combine (i) high productivities at elevated temperatures and pressures in the presence of hydrogen as a molecular weight control agent, and (ii) high levels of branching, are especially sought. New catalysts and processes for these purposes are described herein.

The distribution of branch lengths obtained using late transition metal catalysts is also important. Previously reported catalysts have tended to give ethylene homopolymers with too few longer branches, relative to methyl branches, to give LLDPE's with adequate film toughness. With the objective of addressing this problem, we have developed catalysts and processes which give ethylene homopolymers with substantially higher ratios of $C_5$ and longer branches to methyl branches. These new catalysts, processes and ethylene homopolymer compositions are also described herein.

SUMMARY OF THE INVENTION

In a first aspect, this invention pertains to a catalyst for olefin polymerization, comprising a Group 3–11 metal complex of a bidentate, tridentate, or tetradentate ligand, wherein the complex comprises at least one N-donor fragment of formula 1a or 1b;

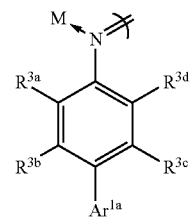

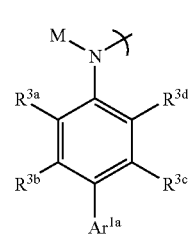

wherein:

M is a Group 3–11 transition metal;

$R^{3a-d}$ are each, independently, H, F, Cl, Br, hydrocarbyl, substituted hydrocarbyl, fluoroalkyl, nitro, heteroatom connected hydrocarbyl or heteroatom connected substituted hydrocarbyl; and $Ar^{1a}$ is an aryl or heteroaryl group substituted at one or both ortho positions by a group $Q^2$; wherein $Q^2$ is hydrocarbyl, substituted hydrocarbyl, heteroatom connected hydrocarbyl or heteroatom connected substituted hydrocarbyl.

In a first preferred embodiment of the first aspect, M is a Group 8–10 metal.

In a second preferred embodiment, M is nickel, and $Q^2$ is sufficiently long to extend sufficiently close to the metal M to increase the catalyst productivity at elevated temperatures, or in the presence of hydrogen, or both, relative to an otherwise similar catalyst wherein $Q^2$ is replaced by H, Me, or Ph.

In a third preferred embodiment, M is nickel, and $Q^2$ is sufficiently long to extend sufficiently close to the metal M to increase the regioselectivity or stereoselectivity of comonomer incorporation, relative to an otherwise similar catalyst wherein $Q^2$ is replaced by H, Me, or Ph.

In a fourth preferred embodiment, M is nickel, and $Q^2$ is sufficiently long to extend sufficiently close to the metal M to decrease the amount of chain-running, relative to an otherwise similar catalyst wherein $Q^2$ is replaced by H, Me, or Ph.

In a fifth preferred embodiment, M is palladium, and $Q^2$ is sufficiently long to extend sufficiently close to the metal M to decrease the amount of chain-running, relative to an otherwise similar catalyst wherein $Q^2$ is replaced by H, Me, or Ph.

In a sixth preferred embodiment, M is nickel, and $Q^2$ is sufficiently long to extend sufficiently close to the metal M to increase the chain-running stereoselectivity, relative to an otherwise similar catalyst wherein $Q^2$ is replaced by H, Me, or Ph.

In a seventh preferred embodiment, M is nickel, and $Q^2$ is sufficiently long to extend sufficiently close to the metal M to decrease the rate of activation of the catalyst when an alkylaluminum reagent is used as cocatalyst, relative to an otherwise similar catalyst wherein $Q^2$ is replaced by H, Me, or Ph.

In an eighth preferred embodiment, M is a Group 8–10 metal and the catalyst comprises a bidentate ligand selected from Set 1;

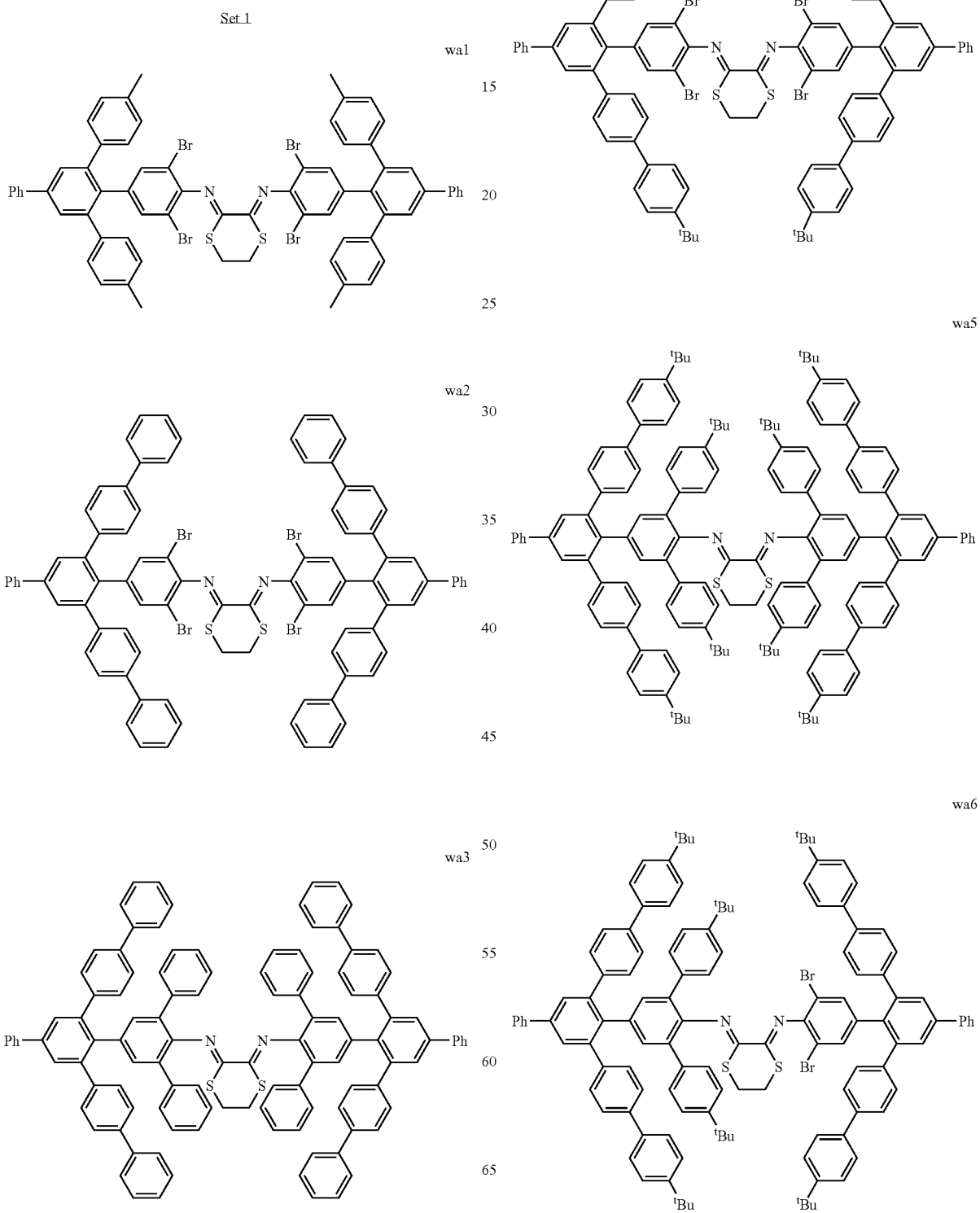

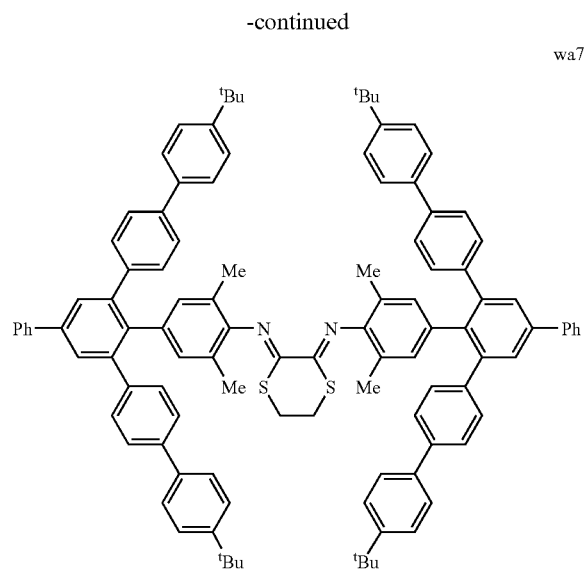
wa7
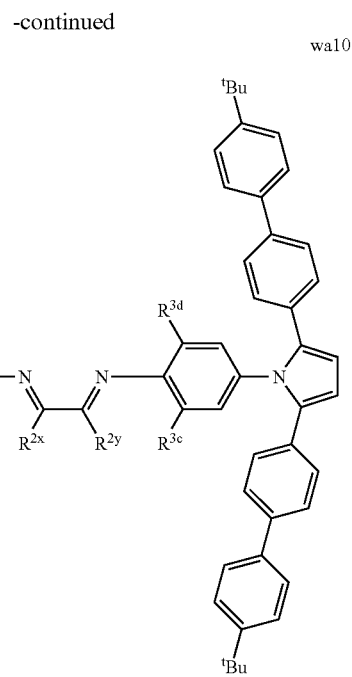
wa10
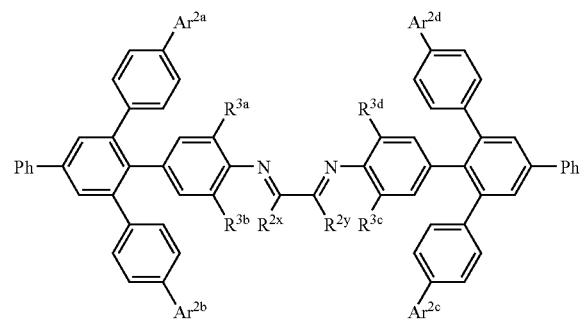
wa8
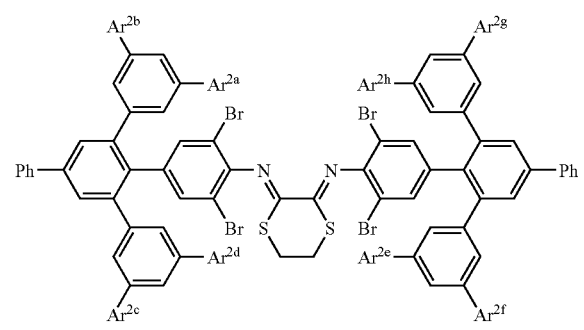
wa9
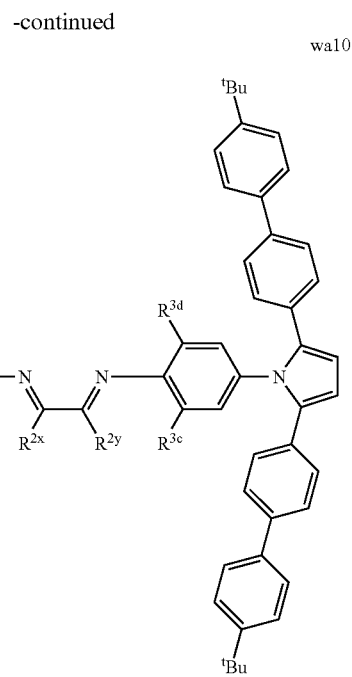
wa11
wa12
wa13

-continued

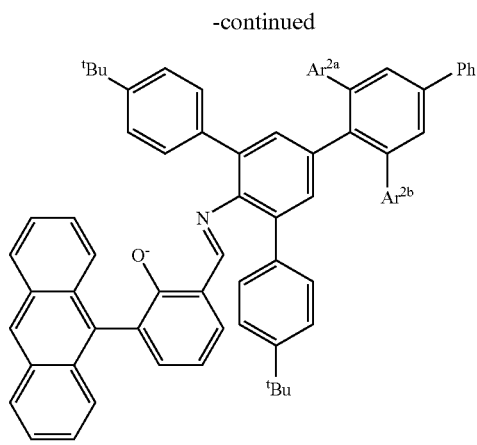

wa14

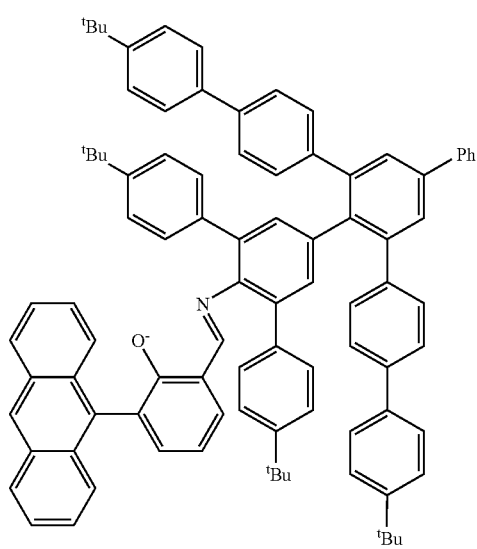

wa15

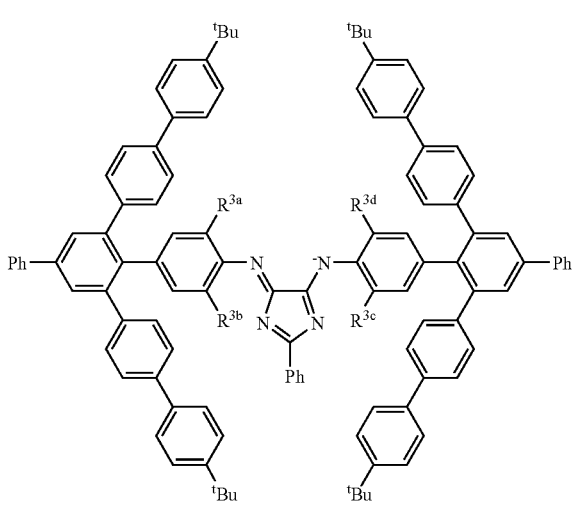

wa16

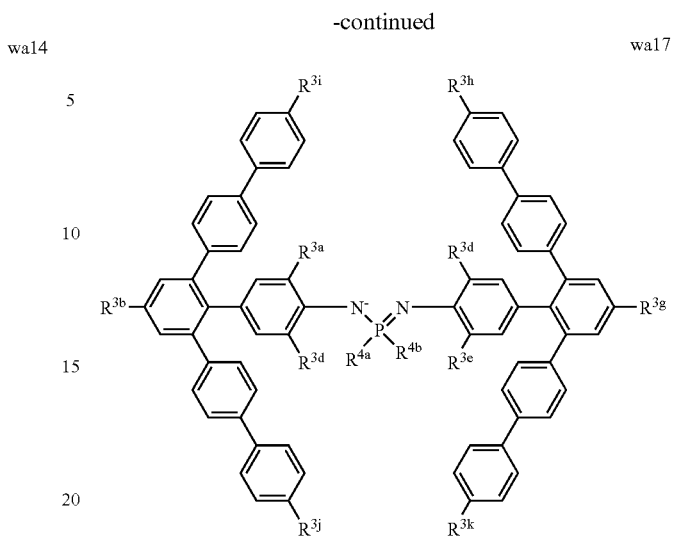

wa17

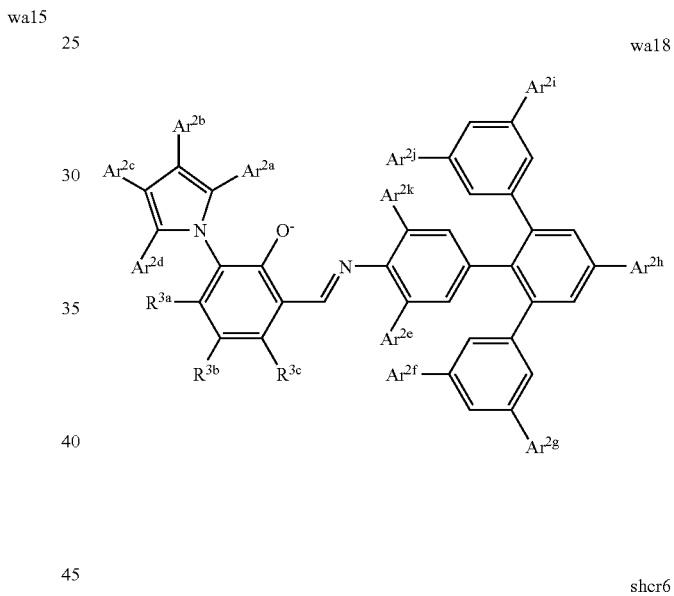

wa18 shcr6 wherein:
$R^{2x,y}$ are each independently H, hydrocarbyl, substituted hydrocarbyl, heteroatom connected hydrocarbyl, heteroatom connected substituted hydrocarbyl; silyl, or ferrocenyl; in addition, $R^{2x}$ and $R^{2y}$ may be linked by a bridging group;
$R^{3a-k}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro;

$R^{4a,b}$ are each independently hydrocarbyl, substituted hydrocarbyl, heteroatom connected hydrocarbyl, heteroatom connected substituted hydrocarbyl; in addition, $R^{4a}$ and $R^{4b}$ may be linked by a bridging group;

"surface" refers to a silicon or other atom which is part of, or attached to, a solid support;

$G^1$ is a divalent bridging group; and $Ar^{2a-m}$ are each independently hydrocarbyl, substituted hydrocarbyl, heteroatom attached hydrocarbyl, heteroatom attached substituted hydrocarbyl, halo, nitro, boryl, or trialkoxysilane.

In a ninth preferred embodiment of this first aspect, M is iron or cobalt, the catalyst comprises a tridentate ligand, and $Q^2$ which is sufficiently long to extend sufficiently close to the metal M to increase the catalyst productivity at elevated temperatures.

In a tenth preferred embodiment, the tridentate ligand of the ninth preferred embodiment of this first aspect is selected from Set 2;

Set 2

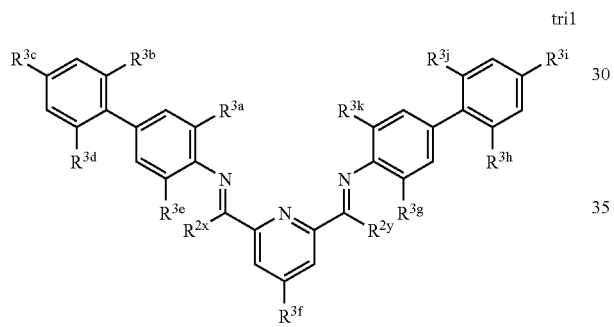

wherein:

$R^{2x,y}$ are each independently H, hydrocarbyl, substituted hydrocarbyl, heteroatom connected hydrocarbyl, heteroatom connected substituted hydrocarbyl; silyl, or ferrocenyl; and $R^{3a-k}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro.

In an eleventh preferred embodiment, the catalyst is a titanium or zirconium complex of a bidentate ligand selected from Set 3;

Set 3

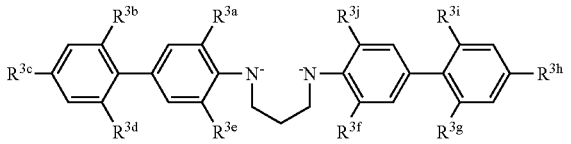

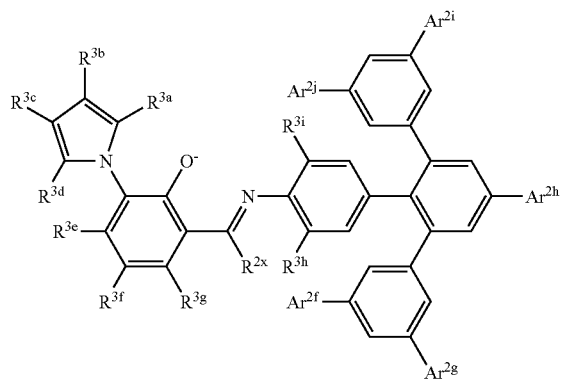

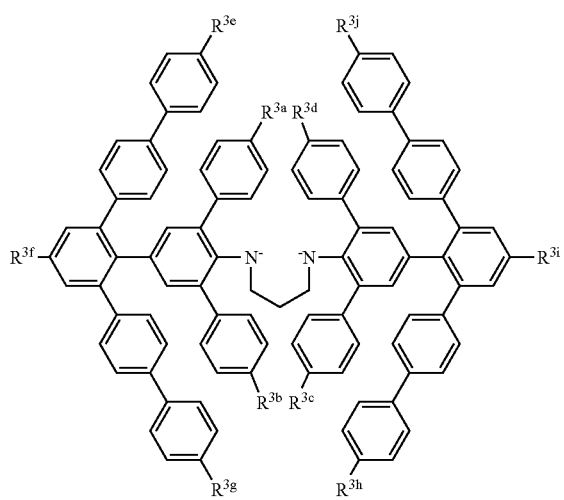

wherein:

$R^{2x}$ is H, hydrocarbyl, substituted hydrocarbyl, heteroatom connected hydrocarbyl, heteroatom connected substituted hydrocarbyl, silyl, or ferrocenyl;

$R^{3a-j}$ are each independently H, hydrocarbyl, substituted hydrocarbyl, heteroatom connected hydrocarbyl, heteroatom connected substituted hydrocarbyl, fluoroalkyl, fluoro, chloro, or bromo; and $Ar^{2a-j}$ are each independently hydrocarbyl, substituted hydrocarbyl, heteroatom attached hydrocarbyl, heteroatom attached substituted hydrocarbyl, halo, nitro, boryl, or trialkoxysilane.

In a twelfth preferred embodiment, the catalyst further comprises a solid support.

In a thirteenth preferred embodiment, the catalyst of the twelfth embodiment is attached to the solid support via a covalent bond to the group $Ar^{1a}$.

In a second aspect, this invention pertains to a process for the polymerization of olefins, comprising contacting one or more olefins with the catalyst of the first aspect.

In a first preferred embodiment of the second aspect, at least one of the olefins is ethylene.

In a second preferred embodiment of the second aspect, the olefin is ethylene, M is nickel, the temperature is at least 80° C., the pressure is less than about 800 psig, sufficient hydrogen is added to reduce the number average molecular weight of the polymer by at least 20% relative to an otherwise similar reaction conducted in the absence of hydrogen, the catalyst productivity is at least 500 kg polyethylene per g nickel, and the polymer has a DSC (Differential Scanning Calorimetry) first cycle peak melting point greater than 131° C.

In a third, more preferred embodiment of the second embodiment of the second aspect, sufficient hydrogen is added to reduce the number average molecular weight of the polymer by at least 50% relative to an otherwise similar reaction conducted in the absence of hydrogen, and the polymer has a DSC first cycle peak melting point greater than 133° C.

In a fourth preferred embodiment of the second aspect, at least one of the olefins is ethylene, M is palladium and the amount of chain running is reduced.

In a third aspect, this invention pertains to a bidentate, tridentate, or tetradentate ligand of the first or second aspects.

In a fourth aspect, this invention pertains to a process for the polymerization of olefins, comprising contacting one or more olefins with a catalyst comprising a Group 8–10 metal complex of a bidentate, N,N-donor ligand, wherein the first of the donor nitrogens, $N^1$, is substituted by an aromatic or heteroaromatic ring wherein the ortho substituents are aryl or heteroaryl groups, and the second of the donor nitrogens, $N^2$, is substituted by an aromatic or heteroaromatic ring wherein one or both of the ortho substituents are other than aryl or heteroaryl; wherein the catalyst is capable of homopolymerizing ethylene to produce a polymer with a number average molecular weight of at least 20,000 g/mole and at least 20 branch points per 1000 carbons with a catalyst productivity of at least 500 kg polyethylene per g of Group 8–10 metal at a temperature of at least 60° C. at a partial pressure of ethylene of at least 350 psia at a partial pressure of hydrogen of at least 2 psia. Preferred substituents other than aryl or heteroaryl include Br, Cl, $CF_3$ and fluoroalkyl.

In a first preferred embodiment of this fourth aspect, the ligand is such that the calculated rate of olefin rotation in square planar complexes of the type (L)M(H) $(R^{1a}CH=CHR^{1b})^{n+}$, wherein n=0 or 1, M is nickel or palladium, L is the bidentate, N,N-donor ligand, $R^{1a}$ is H or Me, and $R^{1b}$ is Me, and $R^{1a}CH=CHR^{1b}$ is trans to $N^1$, is at least 2 times higher than the calculated rate of olefin rotation in the complex wherein $R^{1a}CH=CHR^{1b}$ is cis to $N^1$.

In a second, more preferred embodiment, the calculated rate of olefin rotation in the complex of the first preferred embodiment of the fourth aspect wherein $R^{1a}CH=CHR^{1b}$ is trans to $N^1$ is at least 4 times higher than the calculated rate of olefin rotation in the isomeric complex wherein $R^{1a}CH=CHR^{1b}$ is cis to $N^1$.

In a third preferred embodiment of this fourth aspect, the metal is nickel, $N^1$ is substituted by a 2,6-diaryl substituted aryl group or a 2,5-diaryl substituted lpyrrolyl group, and $N^2$ is substituted by an aromatic or heteroaromatic ring wherein one or both of the ortho substituents are other than aryl or heteroaryl.

In a fourth, more preferred embodiment of this fourth aspect, the metal is nickel, $N^1$ is substituted by a 2,6-diaryl substituted aryl group, $N^2$ is substituted by an aromatic ring wherein one or both of the ortho substituents are other than aryl or heteroaryl, and the catalyst productivity is at least 500 kg polyethylene per g nickel at a temperature of at least 70° C.

In a fifth preferred embodiment of the fourth aspect, the process of the fourth preferred embodiment of the fourth aspect comprises a catalyst wherein $N^2$ is substituted by an aromatic ring wherein one of the ortho substituents is aryl, heteroaryl or bromo, and the other ortho substituent is bromo.

In a sixth embodiment of the fourth aspect, the bidentate ligand is selected from Set 4;

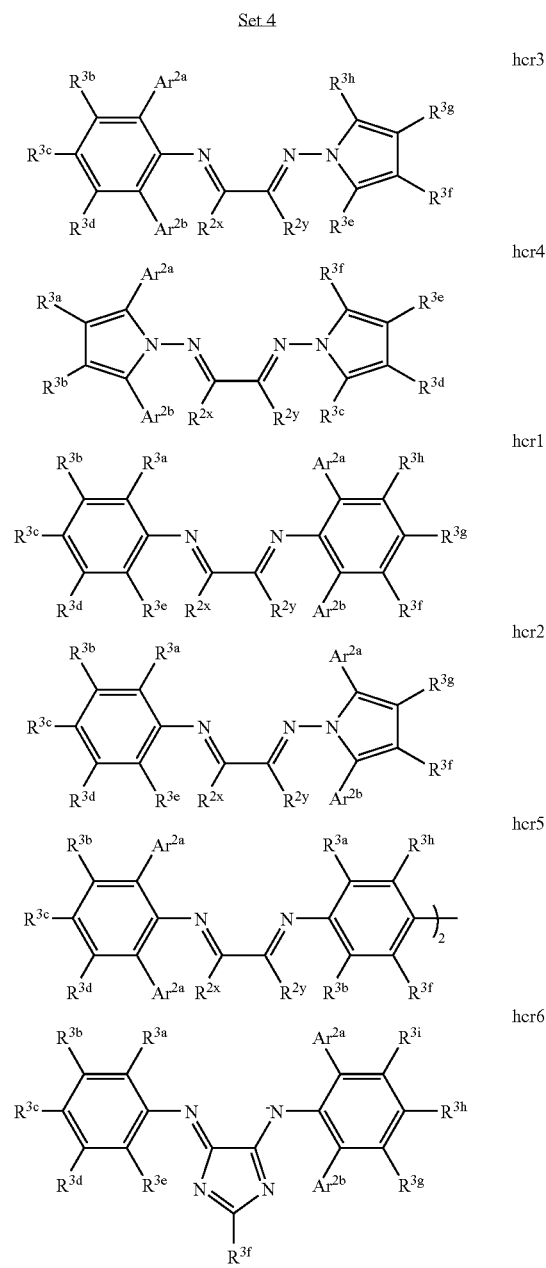

-continued
hcr7
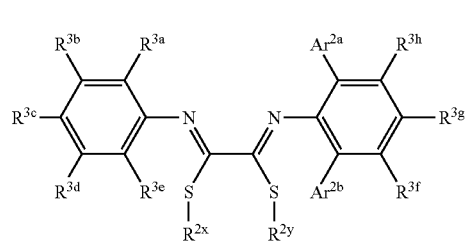
hcr8
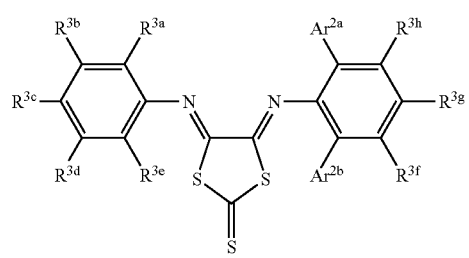
hcr9
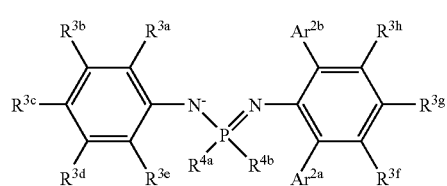
hcr10
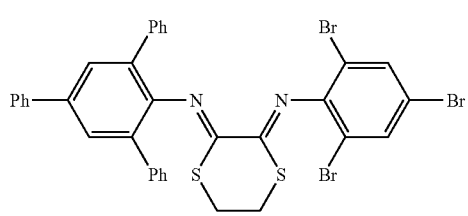
hcr11
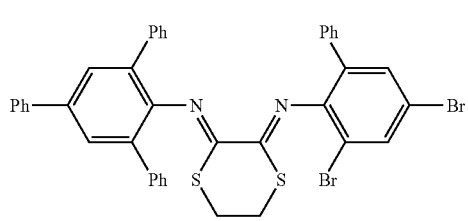
hcr12
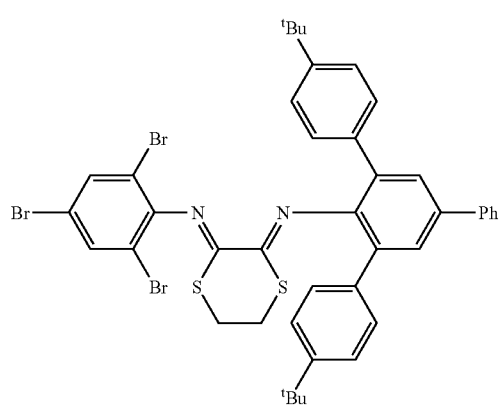
-continued
hcr13
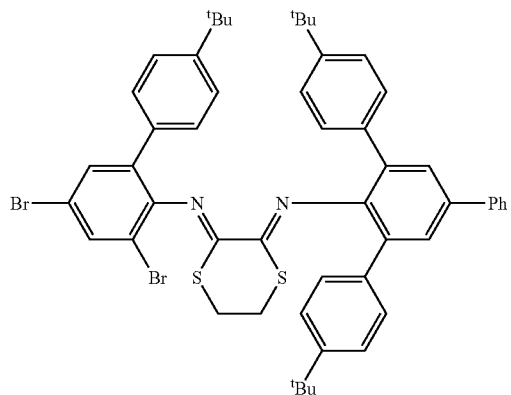
hcr14
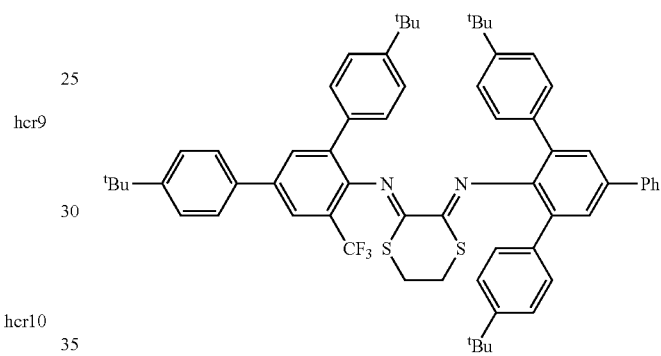
hcr15
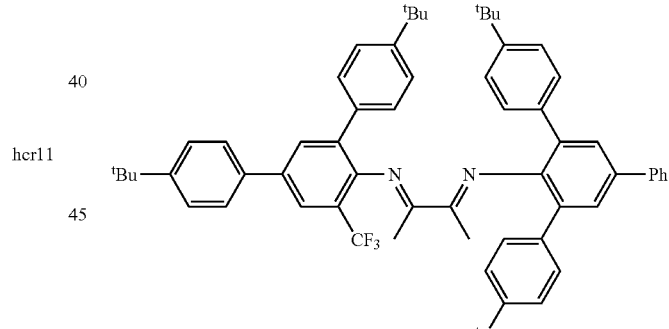
hcr16
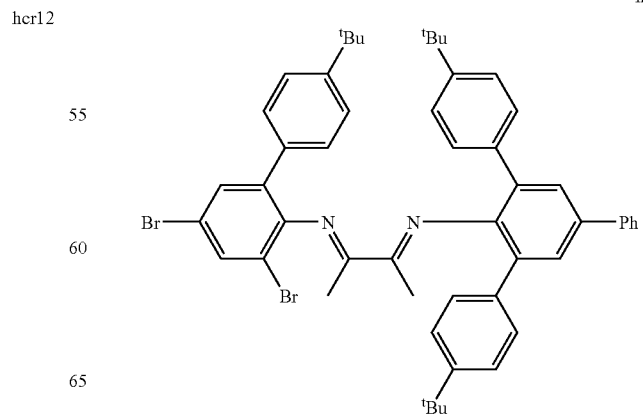

-continued
hcr17
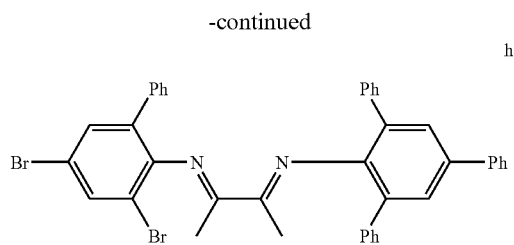
hcr18
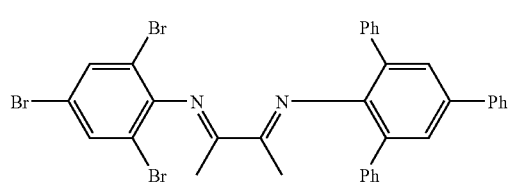
shcr1
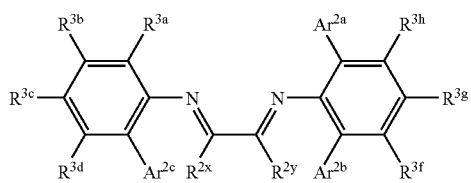
shcr2
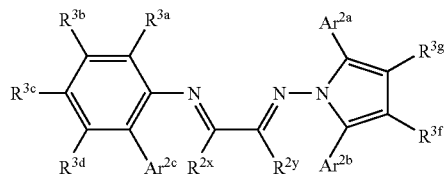
shcr3
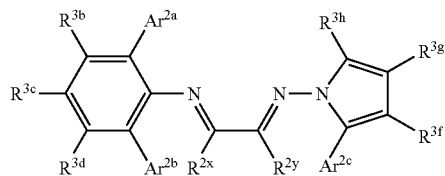
shcr4
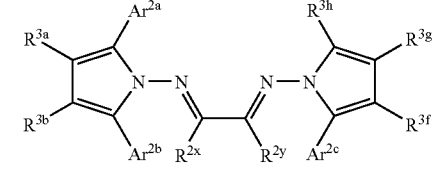
shcr5
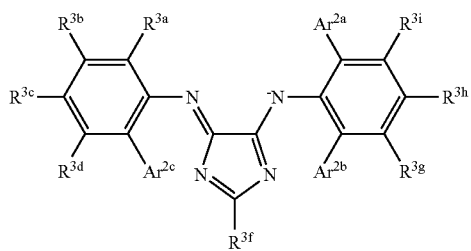
-continued
wa6
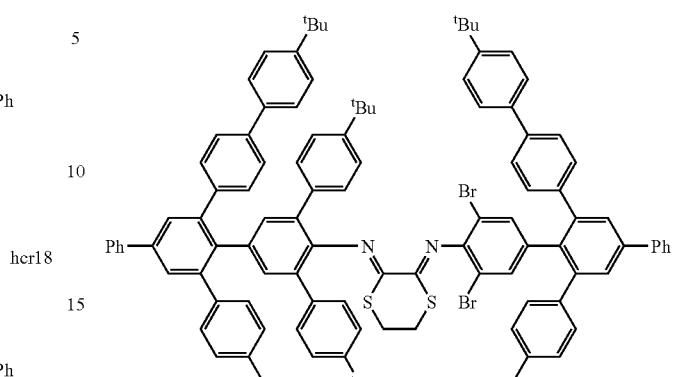
shcr6
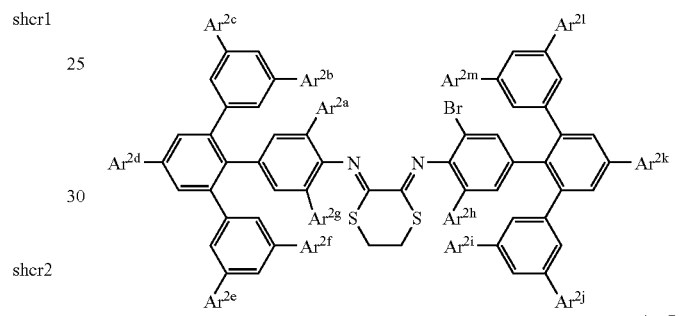
shcr7
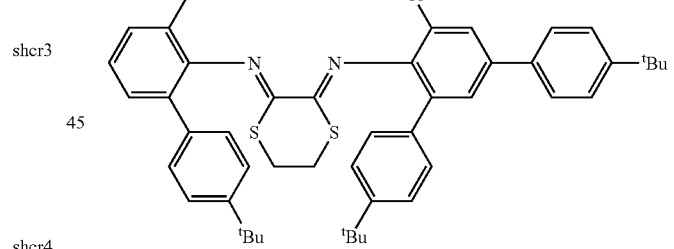
shcr8
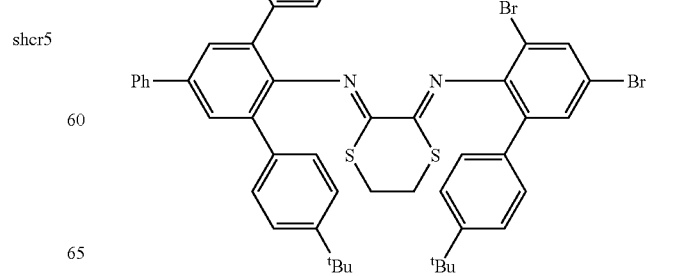

-continued

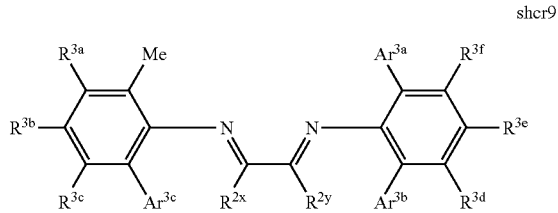

shcr9

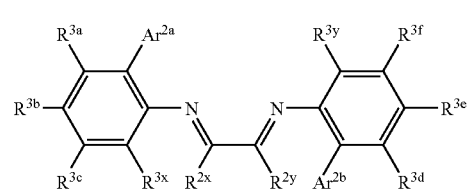

2a wherein:

$R^{2x,y}$ are each independently H, hydrocarbyl, substituted hydrocarbyl, heteroatom connected hydrocarbyl, heteroatom connected substituted hydrocarbyl, silyl, or ferrocenyl; in addition, $R^{2x}$ and $R^{2y}$ may be linked by a bridging group;

$R^{3a-i}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro;

$Ar^{2a-m}$ are each independently aryl or heteroaryl; and $Ar^{3a-c}$ are each independently 4-substituted aryl groups; wherein the 4-substituents are selected from the group consisting of hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, phenylsulfonyl, and nitro.

In a seventh preferred embodiment of the fourth aspect, the olefin is ethylene and the polymer is an ethylene homopolymer wherein the average spacing between branch points is such that there is at least a 10% excess of sequences of the type —CHR—$(CH_2)_{4n+2}$—CHR—, where R is alkyl and n is 0 or a positive integer, relative to sequences of the type —CHR—$(CH_2)_{2m}$—CHR—, where R is alkyl and m is a positive integer.

In an eighth preferred embodiment of the fourth aspect, the olefin is ethylene, $N^2$ is substituted by a 2-aryl-6-bromo-aryl group and the polymer is an ethylene homopolymer wherein there is an excess of isotactic sequences of the type —$CHR^{1a}$—$(CH_2)_{4n+2}$—$CHR^{1b}$—, where $R^{1a}$ and $R^{1b}$ are hydrocarbyl or substituted hydrocarbyl branches and n is 0 or 1, relative to a random distribution.

In a fifth aspect, this invention pertains to a polymer prepared according to the process of the fourth aspect.

In a sixth aspect, this invention pertains to a process for the polymerization of olefins, comprising contacting one or more olefins with a catalyst comprising a Group 8–10 metal complex of a bidentate, tridentate or multidentate ligand, wherein the catalyst is activated using an alkylaluminum compound, wherein the alkylaluminum compound is subsequently selectively deactivated before the bulk of the polymerization has occurred.

In a first preferred embodiment of the sixth aspect, the alkylaluminum compound is selectively deactivated through the addition of a phenol or substituted phenol.

In a second preferred embodiment of the sixth aspect, the Group 8–10 metal complex is a cationic nickel complex of a bidentate N,N-donor ligand.

In a third preferred embodiment of the sixth aspect, the Group 8–10 metal complex is a cationic iron or cobalt complex of a tridentate ligand.

In a seventh aspect, this invention pertains to a catalyst for the polymerization of olefins, comprising a nickel complex of a ligand of formula 2a;

wherein:

$R^{2x,y}$ are each independently hydrocarbyl, substituted hydrocarbyl, heteroatom connected hydrocarbyl, heteroatom connected substituted hydrocarbyl, or silyl; in addition, $R^{2x}$ and $R^{2y}$ may be linked by a bridging group;

$R^{3a-f}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, iodo, cyano, or nitro;

$R^{3x,y}$ are each independently halo or fluoroalkyl; and $Ar^{2a,b}$ are each independently aryl or heteroaryl.

In a first preferred embodiment of this seventh aspect, $R^{2x}$ and $R^{2y}$ are linked by a bridging group.

In an eighth aspect, this invention pertains to a process for the polymerization of olefins comprising contacting ethylene and optionally other olefins with the catalyst of the seventh aspect in the presence of sufficient hydrogen to reduce the number average molecular weight of the polymer by at least 10% relative to an otherwise similar process carried out in the absence of hydrogen.

By "other olefins", we mean 1-alkenes, preferably 1-butene, 1-hexene or 1-octene, or long chain 1-alkene macromonomers.

In a ninth aspect, this invention pertains to an ethylene homopolymer having a number average molecular weight of at least 10,000 g/mole, total branching of less than about 70 branches per 1000 carbons, at least 10% saturated hydrocarbon polymer chains, and a ratio of $C_5$ and longer branches to methyl branches of at least 0.35.

In a first preferred embodiment of this ninth aspect, the total branching is less than about 60 branches per 1000 carbons; at least 25% of the polymer chains are saturated hydrocarbon chains; and the ratio of $C_5$ and longer branches to methyl branches is at least 0.40. In a second preferred embodiment, the total branching is less than about 60 branches per 1000 carbons; and the ratio of $C_5$ and longer branches to methyl branches is at least 0.45. In a third preferred embodiment, the Differential Scanning Calorimetry (DSC) curve of the homopolymer shows a bimodal melt endotherm on the second heat from the melt, with the area of the smaller of the two peaks representing at least 25% of the total melt endotherm.

DETAILED DESCRIPTION OF THE INVENTION

In this disclosure, symbols ordinarily used to denote elements in the Periodic Table and commonly abbreviated groups, take their ordinary meaning, unless otherwise specified. Thus, N, O, S, P, and Si stand for nitrogen, oxygen, sulfur, phosphorus, and silicon, respectively, while Me, Et, Pr, $^i$Pr, Bu, $^t$Bu and Ph stand for methyl, ethyl, propyl, iso-propyl, butyl, tert-butyl and phenyl, respectively.

A "1-pyrrolyl or substituted 1-pyrrolyl" group refers to a group of formula II below:

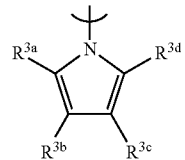

wherein $R^{3a-d}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two or more of $R^{3a-d}$ may be linked by a bridging group or groups to form bicyclic or polycyclic ring systems including carbazol-9-yl and indol-1-yl.

A "hydrocarbyl" group means a monovalent or divalent, linear, branched or cyclic group which contains only carbon and hydrogen atoms. Examples of monovalent hydrocarbyls include the following: $C_1$–$C_{20}$ alkyl; $C_1$–$C_{20}$ alkyl substituted with one or more groups selected from $C_1$–$C_{20}$ alkyl, $C_3$–$C_8$ cycloalkyl, and aryl; $C_3$–$C_8$ cycloalkyl; $C_3$–$C_8$ cycloalkyl substituted with one or more groups selected from $C_1$–$C_{20}$ alkyl, $C_3$–$C_8$ cycloalkyl, and aryl; $C_6$–$C_{14}$ aryl; and $C_6$–$C_{14}$ aryl substituted with one or more groups selected from $C_1$–$C_{20}$ alkyl, $C_3$–$C_8$ cycloalkyl, and aryl. Examples of divalent (bridging) hydrocarbyls include: —$CH_2$—, —$CH_2CH_2$—, —$CH_2CH_2CH_2$—, and 1,2-phenylene.

The term "aryl" refers to an aromatic carbocyclic monoradical, which may be substituted or unsubstituted, wherein the substituents are halo, hydrocarbyl, substituted hydrocarbyl, heteroatom attached hydrocarbyl, heteroatom attached substituted hydrocarbyl, nitro, cyano, fluoroalkyl, sulfonyl, and the like. Examples include: phenyl, naphthyl, anthracenyl, phenanthracenyl, 2,6-diphenylphenyl, 3,5-dimethylphenyl, 4-nitrophenyl, 3-nitrophenyl, 4-methoxyphenyl, 4-dimethylaminophenyl, 2,6-dibromophenyl, 2,4,6-tribromophenyl, 2,4-dibromo-6-phenylphenyl, 2,6-di(4-tert-butylphenyl)phenyl, 2,6-di(4-tert-butylphenyl)-4-phenylphenyl, 2,6-di(4-phenylphenyl)-4-phenylphenyl, 2,4-dibromo-6-trifluoromethylphenyl, 2,4-bis(4-tert-butylphenyl)-6-trifluoromethylphenyl, 2-chloro-4,6-di(4-tert-butylphenyl)phenyl, 2,6-di(1-naphthyl)-4-phenylphenyl, and the like.

A "heterocyclic ring" refers to a carbocyclic ring wherein one or more of the carbon atoms has been replaced by an atom selected from the group consisting of O, N, S, P, Se, As, Si, B, and the like.

A "heteroaromatic ring" refers to an aromatic heterocyclic ring; examples include pyrrole, furan, thiophene, indene, imidazole, oxazole, isoxazole, carbazole, thiazole, pyrimidine, pyridine, pyridazine, pyrazine, benzothiophene, and the like.

A "heteroaryl" refers to a heterocyclic ring monoradical which is aromatic; examples include 1-pyrrolyl, 2-pyrrolyl, 3-pyrrolyl, furyl, thienyl, indenyl, imidazolyl, oxazolyl, isoxazolyl, carbazolyl, thiazolyl, pyrimidinyl, pyridyl, pyridazinyl, pyrazinyl, benzothienyl, and the like, and substituted derivatives thereof.

A "silyl" group refers to a $SiR_3$ group wherein Si is silicon and R is hydrocarbyl, substituted hydrocarbyl, heteroatom connected hydrocarbyl, or silyl, as in $Si(SiR_3)_3$.

A "boryl" group refers to a $BR_2$ or $B(OR)_2$ group, wherein R is hydrocarbyl or substituted hydrocarbyl.

A "heteroatom" refers to an atom other than carbon or hydrogen. Preferred heteroatoms include oxygen, nitrogen, phosphorus, sulfur, selenium, arsenic, chlorine, bromine, silicon, and fluorine.

A "substituted hydrocarbyl" refers to a monovalent, divalent, or trivalent hydrocarbyl substituted with one or more heteroatoms. Examples of monovalent substituted hydrocarbyls include: 2,6-dimethyl-4-methoxyphenyl, 2,6-diisopropyl-4-methoxyphenyl, 4-cyano-2,6-dimethylphenyl, 2,6-dimethyl-4-nitrophenyl, 2,6-difluorophenyl, 2,6-dibromophenyl, 2,6-dichlorophenyl, 4-methoxycarbonyl-2,6-dimethylphenyl, 2-tert-butyl-6-chlorophenyl, 2,6-dimethyl-4-phenylsulfonylphenyl, 2,6-dimethyl-4-trifluoromethylphenyl, 2,6-dimethyl-4-trimethylammoniumphenyl (associated with a weakly coordinated anion), 2,6-dimethyl-4-hydroxyphenyl, 9-hydroxyanthr-10-yl, 2-chloronapth-1-yl, 4-methoxyphenyl, 4-nitrophenyl, 9-nitroanthr-10-yl, —$CH_2OCH_3$, cyano, trifluoromethyl, and fluoroalkyl. Examples of divalent (bridging) substituted hydrocarbyls include: 4-methoxy-1,2-phenylene, 1-methoxymethyl-1,2-ethanediyl, 1,2-bis(benzyloxymethyl)-1,2-ethanediyl, and 1-(4-methoxyphenyl)-1,2-ethanediyl.

A "heteroatom connected hydrocarbyl" refers to a group of the type $E^{10}$(hydrocarbyl), $E^{20}$H(hydrocarbyl), or $E^{20}$(hydrocarbyl)$_2$, where $E^{10}$ is an atom selected from Group 16 and $E^{20}$ is an atom selected from Group 15. A "heteroatom connected substituted hydrocarbyl" refers to a group of the type $E^{10}$(substituted hydrocarbyl), $E^{20}$H(substituted hydrocarbyl), or $E^{20}$(substituted hydrocarbyl)$_2$, where $E^{10}$ is an atom selected from Group 16 and $E^{20}$ is an atom selected from Group 15.

The term "fluoroalkyl" as used herein refers to a $C_1$–$C_{20}$ alkyl group substituted by one or more fluorine atoms.

An "olefin" refers to a compound of the formula $R^{1a}CH=CHR^{1b}$, where $R^{1a}$ and $R^{1b}$ may independently be H, hydrocarbyl, substituted hydrocarbyl, fluoroalkyl, silyl, O(hydrocarbyl), or O(substituted hydrocarbyl), and where $R^{1a}$ and $R^{1b}$ may be connected to form a cyclic olefin, provided that in all cases, the substituents $R^{1a}$ and $R^{1b}$ are compatible with the catalyst. In the case of most Group 4–7 catalysts, this will generally mean that the olefin should not contain good Lewis base donors, since this will tend to severely inhibit catalysis. Preferred olefins for such catalysts include ethylene, propylene, butene, hexene, octene, cyclopentene, norbornene, and styrene. In the case of the Group 8–10 catalysts, Lewis basic substituents on the olefin will tend to reduce the rate of catalysis in most cases; however, useful rates of homopolymerization or copolymerization can nonetheless be achieved with some of those olefins. Preferred olefins for such catalysts include ethylene, propylene, butene, hexene, octene, and fluoroalkyl substituted olefins, but may also include, in the case of palladium and some of the more functional group tolerant nickel catalysts, norbornene, substituted norbornenes (e.g., norbornenes substituted at the 5-position with halide, siloxy, silane, halo carbon, ester, acetyl, alcohol, or amino groups), cyclopentene, ethyl undecenoate, acrylates, vinyl ethylene carbonate, 4-vinyl-2,2-dimethyl-1,3-dioxolane, and vinyl acetate.

In some cases, the Group 8–10 catalysts can be inhibited by olefins which contain additional olefinic or acetylenic functionality. This is especially likely if the catalyst is prone to "chain-running" wherein the catalyst can migrate up and down the polymer chain between insertions, since this can lead to the formation of relatively unreactive π-allylic intermediates when the olefin monomer contains additional unsaturation. Such effects are best determined on a case-by-case basis, but may be predicted to some extent through knowledge of how much branching is observed with a given catalyst in ethylene homopolymerizations; those catalysts which tend to give relatively high levels of branching with ethylene will tend to exhibit lower rates when short chain diene co-monomers are used under the same conditions. Longer chain dienes tend to be less inhibitory than shorter chain dienes, when other factors are kept constant, since the catalyst has to migrate farther to form the π-allyl, and another insertion may intervene first. Similar considerations apply to unsaturated esters which are capable of inserting and chain-running to form relatively stable intramolecular chelate structures wherein the Lewis basic ester functionality occupies a coordination site on the catalyst. In such cases, short chain unsaturated esters, such as methyl acrylate, tend to be more inhibitory than long chain esters, such as ethyl undecenoate, if all other factors are kept constant.

By "alpha-olefin functional comonomer" we mean an alpha-olefin which contains a functional group containing at least one N or O atom. Preferred functional groups include esters, alkyl ethers, carbonates and nitriles.

The term "ortho" is used to refer to substituents attached to the 2- and 6-positions of a 1-attached, six-membered aromatic or heteroaromatic ring, or the 2- and 5-positions of a 1-attached, five-membered aromatic or heteroaromatic ring, or more generally the first substitutable positions on either side of the point of attachment of said aromatic or heteroaromatic ring to said donor nitrogen.

By "chain running", we mean the process by which certain olefin polymerization catalysts, especially those based on Group 8–10 transition metal complexes of bidentate ligands, are capable of migrating along a growing polymer chain between insertion events to form branched polymers from ethylene alone, and give modes of enchainment other than 1,2 enchainment when substituted alkenes are polymerized or copolymerized.

By "olefin rotation", we mean rotation by at least 180° about a vector extending from said Group 8–10 metal to the olefin centroid. The rate of olefin rotation may be calculated using Density Field Theory/Molecular Mechanics programs (c.f. Ziegler et al. in *J. Am. Chem. Soc.* 1997, 119, 1094 and 6177).

By "isotactic sequences of the type —CHR$^{1a}$—(CH$_2$)$_{4n+2}$—CHR$^{1b}$—", we mean polymer chain sequences of the type —CHR$^{1a}$—CH$_2$—CH$_2$—CHR$^{1b}$— or —CHR$^{1a}$—(CH$_2$)$_6$—CHR$^{1b}$— in which the configuration about the —CHR$^{1a}$— center is the same as that about the —CHR$^{1b}$— center where R$^{1a}$ and R$^{1b}$ are hydrocarbyl or substituted hydrocarbyl branches and n is 0 or 1. When the only olefin monomer is ethylene, the most common type of branch will be methyl with most of the catalysts of the current invention; however, longer branches will also be present in most cases, especially when the total number of branches is greater than about 10 per 1000 carbons.

By "different (a) comonomer incorporation selectivities, (b) chain running rates, (c) stereoselectivities, or (d) combinations thereof," we mean a difference of at least 10%, preferably at least 20%, more preferably at least 40%.

By "increase the catalyst productivity at elevated temperatures, or in the presence of hydrogen, or both", we mean a catalyst productivity, expressed in units of kg polymer per mmole catalyst, which is at least 25% higher, preferably 50% higher, even more preferably 100% higher than that observed with an otherwise similar catalyst with H, Me or Ph in place of group Ar$^{1a}$, under the same reaction conditions.

By "elevated temperatures", we mean a temperature of at least 60° C., preferably at least 70° C., even more preferably at least 80° C.

By "in the presence of hydrogen", we mean an amount of hydrogen sufficient to reduce the number average molecular weight by at least 5%, preferably at least 10%, even more preferably at least 20%, relative to an otherwise similar reaction conducted in the absence of hydrogen.

By "increase the regioselectivity or stereoselectivity of comonomer incorporation", we mean an increase of at least 10%, preferably at least 20% in either the regioselectivity or stereoselectivity of comonomer incorporation, relative to that observed for an otherwise similar catalyst with H, Me or Ph in place of group Ar$^{1a}$, under the same reaction conditions.

By "reduce the amount of chain running", we mean either a decrease of at least 10%, preferably at least 20%, in the amount of branching observed for a branched polyolefin derived from ethylene alone, or an increase of at least 10%, preferably at least 20%, in the amount of branching observed for a chain-straightened poly-alpha-olefin, relative to that observed for an otherwise similar catalyst with H, Me or Ph in place of group Ar$^{1a}$, under the same reaction conditions.

By "chain-straightened", we mean a poly-alpha-olefin with fewer branches than would be observed using an olefin polymerization catalyst which cannot undergo chain-running.

By "increase the chain-running stereoselectivity", we mean an increase of at least 10%, preferably at least 20% in the occurrence of configurational correlation between adjacent substituted carbons along the polymer chain, relative to a purely random distribution.

By "decrease the rate of activation of the catalyst", we mean the catalyst precursor is converted into active form more slowly than would be observed for otherwise similar catalysts with H, Me or Ph in place of group Ar$^{1a}$, under the same reaction conditions. Such slower activation can be advantageous under certain circumstances, including, for example, gas phase fluidized bed processes, where overly rapid activation can lead to over-heating of supported catalyst particles and reactor fouling.

The term "alpha-olefin" is used to refer to an olefin of formula H$_2$C═CHR, where R is a hydrocarbyl group. Preferred alpha-olefins are those with 3–40 carbons. A "π-allyl" group refers to a monoanionic group with three sp$^2$ carbon atoms bound to a metal center in a η$^3$-fashion. Any of the three sp$^2$ carbon atoms may be substituted with a hydrocarbyl, substituted hydrocarbyl, heteroatom connected hydrocarbyl, heteroatom connected substituted hydrocarbyl, or O-silyl group.

Examples of π-allyl groups include:

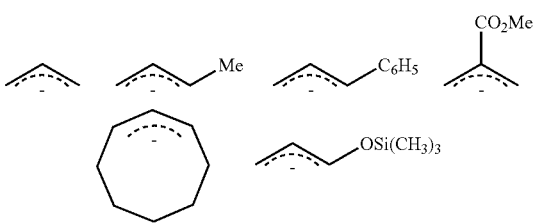

The term π-benzyl group denotes an π-allyl group where two of the sp² carbon atoms are part of an aromatic ring. Examples of π-benzyl groups include:

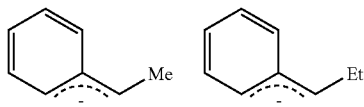

A "bridging group" refers to an atom or group which links two or more groups, which has an appropriate valency to satisfy its requirements as a bridging group, and which is compatible with the desired catalysis. Suitable examples include divalent or trivalent hydrocarbyl, substituted hydrocarbyl, heteroatom connected hydrocarbyl, heteroatom connected substituted hydrocarbyl, substituted silicon(IV), boron(III), N(III), P(III), and P(V), —C(O)—, —SO₂—, —C(S)—, —B(OMe)—, —C(O)C(O)—, O, S, and Se. In some cases, the groups which are said to be "linked by a bridging group" are directly bonded to one another, in which case the term "bridging group" is meant to refer to that bond. By "compatible with the desired catalysis," we mean the bridging group either does not interfere with the desired catalysis, or acts to usefully modify the catalyst activity or selectivity.

The term "weakly coordinating anion" is well known in the art per se and generally refers to a large bulky anion capable of delocalization of the negative charge of the anion. The importance of such delocalization depends to some extent on the nature of the transition metal comprising the cationic active species, with the Group 4–6 transition metals requiring less coordinating anions, such as $B(C_6F_5)_4^-$, than many Group 8–10 transition metal based catalysts, which can in some cases give active catalysts with $BF_4^-$ counteranions. Weakly coordinating anions, not all of which would be considered bulky, include, but are not limited to: $B(C_6F_5)_4^-$, $PF_6^-$, $BF_4^-$, $SbF_6^-$, $(Ph)_4B^-$ wherein Ph=phenyl, and $Ar_4B^-$ wherein $Ar_4B^-$=tetrakis[3,5-bis(trifluoromethyl)phenyl]-borate. The weakly coordinating nature of such anions is known and described in the literature (S. Strauss et al., Chem. Rev., 1993, 93, 927).

The abbreviation "acac" refers to acetylacetonate. In general, substituted acetylacetonates, wherein one or more hydrogens in the parent structure have been replaced by a hydrocarbyl, substituted hydrocarbyl, or fluoroalkyl, may be used in place of the "acac". Hydrocarbyl substituted acetylacetonates may be preferred in some cases when it is important, for example, to improve the solubility of a (ligand)Ni(acac)BF₄ salt in mineral spirits.

By "under the same reaction conditions", we mean the catalyst loading, solvent, solvent volume, agitation, ethylene pressure, co-monomer concentration, reaction time, and other process relevant parameters are sufficiently similar that a valid comparison can be made between two catalysts.

The phrase "one or more olefins" refers to the use of one or more chemically different olefin monomer feedstocks, for example, ethylene and propylene.

A variety of protocols may be used to generate active polymerization catalysts comprising transition metal complexes of various nitrogen, phosphorous, oxygen and sulfur donor ligands. Examples include (i) the reaction of a Group 4 metallocene dichloride with MAO, (ii) the reaction of a Group 4 metallocene dimethyl complex with N,N-diethylanilinium tetrakis(pentafluorophenyl)borate, (iii) the reaction of a Group 8 or 9 metal dihalide complex of a tridentate N-donor ligand with an alkylaluminum reagent, (iv) the reaction of a Group 8 or 9 metal dialkyl complex of a tridentate N-donor ligand with MAO or HB(3,5-bis(trifluoromethyl)phenyl)₄, (v) the reaction of $(Me_2N)_4Zr$ with 2 equivalents of an N-pyrrol-1-ylsalicylimine, followed by treatment of the product of that reaction with $Me_3SiCl$ and then a triisobutylaluminum-modified methylaluminoxane, and (vi) the reaction of a nickel or palladium dihalide complex of a bidentate N-donor ligand with an alkylaluminum reagent. Additional methods described herein include the reaction of (tridentate N-donor ligand)M(acac)B(C₆F₅)₄ salts with an alkylaluminum reagent, where M is Fe(II) or Co(II), and the reaction of (bidentate N-donor ligand)Ni(acac)X salts with an alkylaluminum reagent, where X is a weakly coordinating anion, such as $B(C_6F_5)_4^-$, $BF_4^-$, $PF_6^-$, $SbF_6^-$, $(F_3CSO_2)_2N^-$, $(F_3CSO_2)_3C^-$, and $OS(O)_2CF_3^-$. Cationic [(ligand)M(π-allyl)]⁺ complexes with weakly coordinating counteranions, where M is a Group 10 transition metal, are often also suitable catalyst precursors, requiring only exposure to olefin monomer and in some cases elevated temperatures (40–100° C.) or added Lewis acid, or both, to form an active polymerization catalyst.

More generally, a variety of $(ligand)_nM(Z^{1a})(Z^{1b})$ complexes, where "ligand" refers to a compound of the present invention, n is 1 or 2, M is a Group 4–10 transition metal, and $Z^{1a}$ and $Z^{1b}$ are univalent groups, or may be taken together to form a divalent group, may be reacted with one or more compounds, collectively referred to as compound Y, which function as co-catalysts or activators, to generate an active catalyst of the form $[(ligand)_nM(T^{1a})(L)]^+X^-$, where n is 1 or 2, $T^{1a}$ is a hydrogen atom or hydrocarbyl, L is an olefin or neutral donor group capable of being displaced by an olefin, M is a Group 4–10 transition metal, and $X^-$ is a weakly coordinating anion. When $Z^{1a}$ and $Z^{1b}$ are both halide, examples of compound Y include: methylaluminoxane (herein MAO) and other aluminum sesquioxides, $R_3Al$, $R_2AlCl$, and $RAlCl_2$ (wherein R is alkyl, and plural groups R may be the same or different). When $Z^{1a}$ and $Z^{1b}$ are both alkyl, examples of a compound Y include: MAO and other aluminum sesquioxides, $R_3Al$, $R_2AlCl$, $RAlCl_2$ (wherein R is alkyl, and plural groups R may be the same or different), $B(C_6F_5)_3$, $R^0_3Sn[BF_4]$ (wherein $R^0$ is hydrocarbyl or substituted hydrocarbyl and plural groups $R^0$ may be the same or different), $H^+X^-$, wherein $X^-$ is a weakly coordinating anion, for example, tetrakis[3,5-bis(trifluoromethyl)phenyl]borate, and Lewis acidic or Bronsted acidic metal oxides, for example, montmorillonite clay. In some cases, for example, when $Z^{1a}$ and $Z^{1b}$ are both halide or carboxylate, sequential treatment with a metal hydrocarbyl, followed by reaction with a Lewis acid, may be required to generate an active catalyst. Examples of metal hydrocarbyls include: MAO, other aluminum sesquioxides, $R_3Al$, $R_2AlCl$, $RAlCl_2$ (wherein R is alkyl, and plural groups R may be the same or different), Grignard reagents, organolithium reagents, and diorganozinc reagents. Examples of Lewis acids include: MAO, other aluminum sesquioxides, $R_3Al$, $R_2AlCl$, $RAlCl_2$ (wherein R is alkyl, and plural groups R may be the same or different), $B(C_6F_5)_3$, $R^0_3Sn[BF_4]$ (wherein $R^0$ is hydrocarbyl or substituted hydrocarbyl and plural groups $R^0$ may be the same or different), and Lewis acidic metal oxides.

The term "alkylaluminum" is used to refer to compounds containing at least one alkyl group bonded to Al(III), which are capable of reacting with a metal complex of the present invention to generate an active olefin polymerization catalyst. In general, this will involve exchanging one or more alkyl groups from the aluminum with a monoanionic atom or group on the metal complex pro-catalyst. In some cases, a hydride may be directly transferred from the β-carbon of the aluminum alkyl to said metal complex. Subsequent abstraction of a second monoanionic atom or group from the metal complex may also be required to generate a cationic active catalyst. When the pro-catalyst is already a cationic metal complex, the role of the alkylaluminum may simply be to exchange an alkyl or hydride from the aluminum with a monoanionic group, such as acetylacetonate, attached to the metal complex. In the case of a cationic π-allyl or π-benzyl pro-catalyst, the alkylaluminum reagent may, in some cases, simply act as a Lewis acid, to promote conversion of the π-allyl or π-benzyl to a σ-allyl or σ-benzyl bonding mode, thereby facilitating binding and insertion of the olefin monomer. When a cationic pro-catalyst is used with an alkylaluminum activator or co-catalyst, it should also be recognized that the starting counteranion (e.g. $BF_4^-$) may react with the alkylaluminum reagent to generate a new counteranion (or a mixture of several different counteranions) under olefin polymerization reaction conditions. Examples of alkylaluminum reagents include: MAO, other aluminum sesquioxides, $Me_3Al$, $EtAlCl_2$, $Et_2AlCl$, $R_3Al$, $R_2AlCl$, $RAlCl_2$ (wherein R is alkyl, and plural groups R may be the same or different), and the like.

The foregoing discussion is intended to illustrate that there are frequently many ways to generate an active catalyst. It is an object of this disclosure to teach that there are a variety of methods wherein the ligands of the present invention can be reacted with a suitable metal precursor, and optionally a co-catalyst, to generate an active olefin polymerization catalyst. Without wishing to be bound by theory, the inventors also believe that the active catalyst typically comprises the catalytically active metal, one or more ligands of the present invention, the growing polymer chain (or a hydride capable of initiating a new chain), and a site on the metal adjacent to the metal-alkyl bond of the chain where ethylene can coordinate, or at least closely approach, prior to insertion. Where specific structures for active catalysts have been implied herein, it should be understood that an object of this invention is to teach and claim that active catalysts comprising the ligands of the present invention are formed as the reaction products of the catalyst activation reactions disclosed herein, regardless of the detailed structures of those active species.

Active catalysts may, in some cases, be generated from more than one oxidation state of a given metal. For example, the present invention describes the use of both Co(III) and Co(II) catalyst precursors to effect olefin polymerization using MAO or other alkylaluminum co-catalysts. Where only one oxidation state of a given metal has been specified herein, it is therefore to be understood that other oxidation states of the same metal, complexed by the ligands of the present invention, can serve as catalyst precursors or active catalysts. When different oxidation state complexes of the ligands are used, appropriate changes in the ancillary ligands or the counteranion must obviously accompany any change in oxidation level to balance the charge. Examples where multiple oxidation state precursors are especially likely to be encountered include, but are not limited to, Ti(III)/Ti(IV), Fe(III)/Fe(II), and Co(III)/Co(II).

The catalysts of the present invention may be used in batch and continuous processes, in solution or slurry or gas phase processes.

In some cases, it is advantageous to attach the catalyst to a solid support. Examples of useful solid supports include: inorganic oxides, such as talcs, silicas, titania, silica/chromia, silica/chromia/titania, silica/alumina, zirconia, aluminum phosphate gels, silanized silica, silica hydrogels, silica xerogels, silica aerogels, montmorillonite clay and silica co-gels, as well as organic support materials such as polystyrene and functionalized polystyrene. (See, for example, S. B. Roscoe et al., "Polyolefin Spheres from Metallocenes Supported on Non-Interacting Polystyrene," 1998, *Science*, 280, 270–273 (1998)).

Thus, in a preferred embodiment, the catalysts of the present invention are attached to a solid support (by "attached to a solid support" is meant ion paired with a component on the surface, adsorbed to the surface or covalently attached to the surface) that has been pre-treated with an alkylaluminum compound. More generally, the alkylaluminum and the solid support can be combined in any order and any number of alkylaluminum(s) can be utilized. In addition, the supported catalyst thus formed may be treated with additional quantities of alkylaluminum. In another preferred embodiment, the compounds of the present invention are attached to silica that has been pre-treated with an alkylaluminum, for example, MAO, $Et_3Al$, $^iBu_3Al$, $Et_2AlCl$, or $Me_3Al$.

Such supported catalysts are prepared by contacting the transition metal compound, in a substantially inert solvent (by which is meant a solvent which is either unreactive under the conditions of catalyst preparation, or if reactive, acts to usefully modify the catalyst activity or selectivity) with MAO-treated silica for a sufficient period of time to generate the supported catalyst. Examples of substantially inert solvents include toluene, o-difluorobenzene, mineral spirits, hexane, $CH_2Cl_2$, and $CHCl_3$.

In another preferred embodiment, the catalysts of the present invention are activated in solution under an inert atmosphere, and then adsorbed onto a silica support which has been pre-treated with a silylating agent to replace surface silanols by trialkylsilyl groups. Methods to pre-treat silicas in this way are known to those skilled in the art and may be achieved, for example, by heating the silica with hexamethyldisilazane and then removing the volatiles under vacuum. A variety of precursors and procedures may be used to generate the activated catalyst prior to said adsorption, including, for example, reaction of a (ligand)Ni(acac)B$(C_6F_5)_4$ complex with $Et_2AlCl$ in a toluene/hexane mixture under nitrogen; where "ligand" refers to a compound of the present invention.

In another, more preferred embodiment, the catalysts of the present invention are covalently attached to a solid support and then activated in a slurry phase process by treatment with an alkylaluminum reagent. Methods of covalent attachment include reaction of a 4-hydroxyphenyl group which is part of the ligand with $Si(NMe_2)_4$, followed by reaction of the resultant ligand-O—$Si(NMe_2)_3$ derivative with silica.

In several cases, metal complexes are depicted herein with square planar, trigonal bipyramidal, or other coordination, however, it is to be understood that no specific geometry is implied.

The polymerizations may be conducted as solution polymerizations, as non-solvent slurry type polymerizations, as slurry polymerizations using one or more of the olefins or other solvent as the polymerization medium, or in the gas phase. One of ordinary skill in the art, with the present disclosure, would understand that the catalyst could be supported using a suitable catalyst support and methods known in the art. Substantially inert solvents, such as toluene, hydrocarbons, methylene chloride and the like, may be used. Propylene and 1-butene are excellent monomers for use in slurry-type copolymerizations and unused monomer can be flashed off and reused.

Temperature and olefin pressure have significant effects on catalyst activity, and on polymer structure, composition, and molecular weight. Suitable polymerization temperatures are preferably from about 20° C. to about 160° C., more preferably 60° C. to about 100° C. Suitable polymerization pressurse range from about 1 bar to about 200 bar, preferably 5 bar to 50 bar, more preferably 10 bar to 50 bar.

The catalysts of the present invention may be used alone, or in combination with one or more other Group 3–10 olefin polymerization or oligomerization catalysts, in solution, slurry, or gas phase processes. Such mixed catalyst systems are sometimes useful for the production of bimodal or multimodal molecular weight or compositional distributions, which may facilitate polymer processing or final product properties.

After the reaction has proceeded for a time sufficient to produce the desired polymers, the polymer can be recovered from the reaction mixture by routine methods of isolation and/or purification.

In general, the polymers of the present invention are useful as components of thermoset materials, as elastomers, as packaging materials, films, compatibilizing agents for polyesters and polyolefins, as a component of tackifying compositions, and as a component of adhesive materials.

High molecular weight resins are readily processed using conventional extrusion, injection molding, compression molding, and vacuum forming techniques well known in the art. Useful articles made from them include films, fibers, bottles and other containers, sheeting, molded objects and the like.

Low molecular weight resins are useful, for example, as synthetic waxes and they may be used in various wax coatings or in emulsion form. They are also particularly useful in blends with ethylene/vinyl acetate or ethylene/methyl acrylate-type copolymers in paper coating or in adhesive applications.

Although not required, typical additives used in olefin or vinyl polymers may be used in the new homopolymers and copolymers of this invention. Typical additives include pigments, colorants, titanium dioxide, carbon black, antioxidants, stabilizers, slip agents, flame retarding agents, and the like. These additives and their use in polymer systems are known per se in the art.

Other features of the invention will become apparent in the following description of working examples, which have been provided for illustration of the invention and are not intended to be limiting thereof.

The molecular weight data presented in the following examples is determined at 135° C. in 1,2,4-trichlorobenzene using refractive index detection, calibrated using narrow molecular weight distribution poly(styrene) standards.

EXAMPLES

Example 1

Ethylene Polymerization at Elevated Temperature and Pressure. General Procedure Used to Obtain the Polymerization Data Given in Table I The data given in Table I was generated using a procedure substantially similar to the following procedure. A 1 L Parr® autoclave, Model 4520, was dried by heating under vacuum to 180° C. at 0.6 torr for 16 h, then cooled and refilled with dry nitrogen. The autoclave was charged with dry, deoxygenated hexane (450 mL) and 1.0 mL of a 10 wt % solution of MAO in toluene (Aldrich®), then purged by pressurizing it to 200 psig with ethylene and venting (3 cycles). Hydrogen was added to the reactor either by direct pressurization to the indicated partial pressure (for hydrogen partial pressures >4 psia), or by pressurizing a 40 mL gas sample loop to 40 or 65 psia with hydrogen, and using ethylene gas to sweep the hydrogen into the reactor (for hydrogen partial pressures $\leq 4$ psia). The autoclave was then heated to the temperature indicated in Table I and pressurized to within about 100 psig of the indicated pressure (see Table I) with ethylene gas while being vigorously stirred. Ethylene pressure was then used to inject 2.0 mL of dry, deoxygenated toluene from a sample loop (to clean the loop), followed by 2.0 mL (corresponding to 0.5 micromole of catalyst) of a toluene stock solution of [(ligand)Ni(acac)][B($C_6F_5$)$_4$], (see Table I for ligand) followed by another 2.0 mL of dry, deoxygenated toluene (to flush the loop), thereby raising the total reactor pressure to 5–10% over the target pressure, after which the reactor was isolated from the ethylene supply and the pressure was allowed to fall to approximately 5–10% below the target pressure, after which more ethylene was added to raise the pressure back to 5–10% over the target pressure and the cycle was repeated as required. In some cases, multiple catalyst injections were made, with the final injection being made at the indicated last injection time. After the indicated total reaction time, 2.0 mL MeOH was injected via the sample loop, and the reactor was promptly cooled, depressurized and opened. The polyethylene product was recovered by filtration, washed with MeOH and then a dilute solution of Irganox™ 1010 (Ciba-Geigy) in acetone, and dried in vacuo at 160° C., 1 mm Hg.

TABLE I

| Entry | Ligand | T (° C.) | Pressure (psig) | $H_2$ (psi) | t (min) | last injection (min) | Yield (g) | Kg PE/ g Ni | mol $C_2H_4$/ mol Ni ($\times 10^{-3}$) | bp per 1000 carbons | $M_n$ ($\times 10^{-3}$) | PDI[1] | $T_m$ (° C.)[2] |
|---|---|---|---|---|---|---|---|---|---|---|---|---|---|
| 1 | hcr10 | 70 | 395 | 2 | 53.3 | 0 | 90.0 | 307 | 634 | 44 | 63.3 | 2.58 | 75.1, 113.6 |
| 2 | wa4 | 70 | 400 | 2 | 175 | 72 | 43.5 | 756 | 1560 | 7.2 | 127.4 | 2.15 | 127.1 |
| 3 | wa4 | 71 | 403 | 2 | 264 | 58 | 24.9 | 859 | 1774 | | | | 129.0 |
| 4 | br4[3,4] | 61 | 420 | 4 | 90 | 0 | 39.0 | 675 | 1393 | | 109.7 | 2.52 | 123.5 |
| 5 | wa6 | 70 | 395 | 1 | 160 | 51 | 31.0 | 538 | 1110 | 27 | 127.2 | 2.05 | 102 |
| 6 | wa6 | 70 | 790 | 1 | 97 | 31 | 38.0 | 644 | 1330 | | | | 122.4 |
| 7 | hcr11 | 70 | 418 | 2 | 160 | 90 | 27.8 | 482 | 994 | | | | 94.9 |
| 8 | wa5 | 80 | 400 | 15 | 31 | 0 | 48.8 | 2054 | 4240 | <1 | 51.4 | 2.2 | 137.7[5], 133.6 |
| 9 | wa5 | 110 | 650 | 16 | 66 | 11 | 29.0 | 610 | 1260 | 7 | 21.8 | 1.99 | 129.2 |
| 10 | ar4[3] | 80 | 397 | 18 | 61 | 0 | 65.5 | 1860 | 3900 | 7 | 40.3 | 1.9 | 127.1 |
| 11 | ar4[3] | 110 | 748 | 17 | 46 | 24 | 19.8 | 411 | 849 | 13 | 30.9 | 1.87 | 121 |

TABLE I-continued

| | | | | | | | | | | | | |
|---|---|---|---|---|---|---|---|---|---|---|---|---|
| 12 | wa4 | 81 | 385 | 0 | 60 | 33 | 20.5 | 355 | 732 | 18.9 | 69.7 | 2.49 | 114.5 |
| 13 | wa4 | 81 | 382 | 0 | 45 | 0 | 12.0 | 414 | 854 | 14.9 | 90.7 | 2.42 | 116.7 |
| 14 | wa4 | 70 | 411 | 3 | 432 | 84 | 23.8 | 819 | 1690 | | 115.5 | 2.29 | 129.0 |
| 15 | wa4 | 70 | 403 | 3 | 264 | 58 | 24.9 | 857 | 1770 | | | | |
| 16 | hcr10 | 71 | 392 | 0 | 53 | 12 | 36.0 | 308 | 636 | 48.8 | 292.1 | 1.98 | 68.6 |
| 17 | hcr12 | 70 | 401 | 2 | 89 | 0 | 64.6 | 373 | 769 | 42 | 83.4 | 3.19 | 76.8, 115.1 |
| 18 | wa6 | 79 | 420 | 0 | 123 | 48 | 15.6 | 270 | 557 | 41.5 | 340.3 | 2.01 | 86.5 |
| 19 | hcr11 | 70 | 418 | 3 | 160 | 90 | 27.8 | 482 | 994 | | | | 94.9 |
| 20 | ill1[6] | 70 | 200 | 5 | 335 | 112 | 21.9 | 184 | 387 | 41 | 13.7 | 1.93 | |
| 21 | hcr11[7] | 80 | 182 | 6 | 107 | 70 | 8.6 | 74 | 153 | 52 | 15.9 | 2.01 | 60.8, 95.1 |
| 22 | shcr10 | 80 | 460 | 7 | 404 | 167 | 31.6 | 309 | 649 | 13.4 | 34.3 | 2.50 | 122.3 |
| 23 | shcr11[8] | 60 | 193 | 7 | 229 | 126 | 46.3 | 399 | 836 | 35 | 35.0 | 2.69 | 80.5, 123 |

Notes:

[1] PDI = polydispersity index = $M_w/M_n$.

[2] 2$^{nd}$ cycle endothermic maximum.

[3] Ligand structure on following page.

[4] AlMe$_3$ (2 mmol) used in place of MAO; 2,6-di-tert-butyl-4-methylphenol (9.1 mmol) injected and allowed to react with the AlMe$_3$ at 80° C. for 30 min prior to addition of the Ni catalyst.

[5] 1$^{st}$ cycle endothermic maximum.

[6] Branches per 1000 carbons by $^{13}$C NMR: 23.2 Me, 3.2 Et, no detected Pr, 1.8 Bu, 12.6 pentyl and longer; ratio C$_5$ and higher to methyl = 0.54.

[7] Branches per 1000 carbons by $^{13}$C NMR: 30.9 Me, 2.6 Et, 3.5 Pr, 0.9 Bu, 13.2 pentyl and longer; ratio C$_5$ and higher to methyl = 0.43.

[8] Branches per 1000 carbons by $^{13}$C NMR: 23.7 Me, 1.8 Et, no detected Pr, no detected Bu, 9.2 pentyl and longer; ratio C$_5$ and higher to methyl = 0.39.

Example 1, cont'd

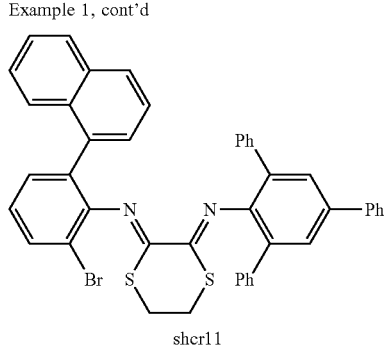

shcr11

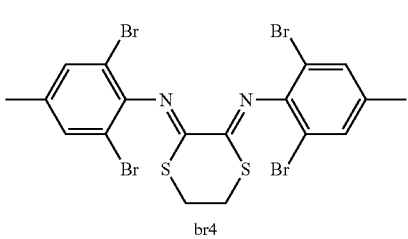

br4

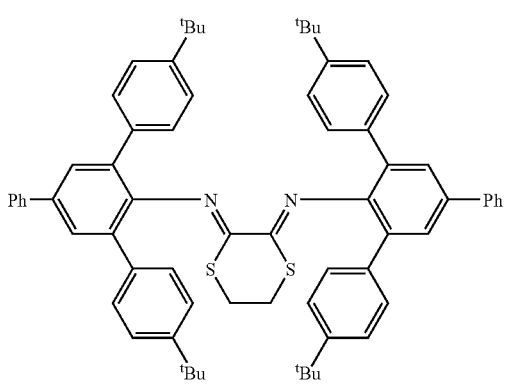

ar4

TABLE I-continued

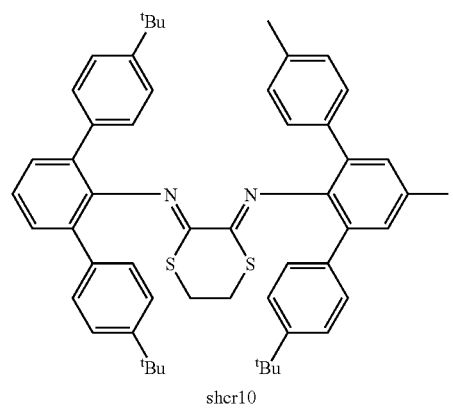

shcr10

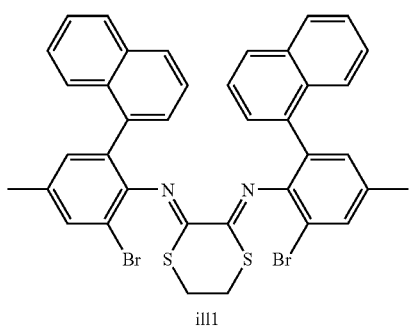

ill1

Example 2

Preparation of da2, a Ti Complex thereof, and Ethylene Polymerization

The requisite aniline is prepared as described for wa5 in Example 19 below and reacts with malonyl dichloride to afford the corresponding bis amide, which is reduced with borane to the diamine. The latter is deprotonated and reacted with $Me_3SiCl$ to afford the bis(trimethylsilyl) derivative, which is converted to the corresponding Ti complex and activated in the presence of ethylene following the method of McConville et al. (*J. Am. Chem. Soc.*, 1996, 118, 10008–10009) to afford polyethylene.

Example 3

Ethylene polymerization using [(w3)Ni(acac)]B($C_6F_5$)$_4$ using MAO to Activate The procedure of Example 1 was followed using 15.72 psi hydrogen, an average reaction temperature of 90° C., an average pressure of 400 psig, two catalyst injections, with the last injection at 0.32 min, and a total reaction time of 120 min to obtain 18.0 g polyethylene, corresponding to 6.1 million mol $C_2H_4$/mol Ni. The reactor pressure was followed as a function of time, and showed an increasing rate of ethylene consumption for the first 20–30 min, after which the rate stabilized and then slowly decreased until the end of the experiment.

Example 4

Ethylene Polymerization using [(w3)Ni(acac)]B($C_6F_5$)$_4$ using $AlMe_3$ to Activate The procedure of Example 3 was followed using 14.7 psi hydrogen and 0.36 mmol $AlMe_3$ in hexane instead of MAO, an average temperature of 81° C., an average pressure of 399 psig, two injections of catalyst, with the last injection at 0.35 min and a total reaction time of 57 min to obtain 49.9 g polyethylene, corresponding to 1.7 million turnovers. A graph of reactor pressure as a function of time showed a more rapid increase in activity than was observed in Example 3, with full activity apparently being reached within about 5 min.

Example 5

Synthesis of wa6-i1

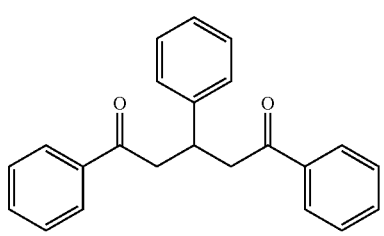

wa6-i1

Benzaldehyde (3.0 g, 28.3 mmol) and 4'-bromoacetophenone (15.0 g, 75.4 mmol) were nearly dissolved in 95% ethanol (60 mL). Solid sodium hydroxide (1 pellet, ca. 100 mg) was added. The mixture was heated at reflux for ca. 30 s, then allowed to cool. Upon cooling, an orange oil settled. The mixture was again heated at reflux for ca. 1 min. Upon cooling, near-colorless crystals separated from the orange supernatant. Ethanol (150 mL) was added, and the large chunky crystals were crushed with a glass rod, then collected by vacuum filtration and washed with ethanol (3×20 mL). The desired diketone wa6-i1 was used without further purification. Crude yield: 10.3 g, 74%.

Example 6

Synthesis of wa6-i2

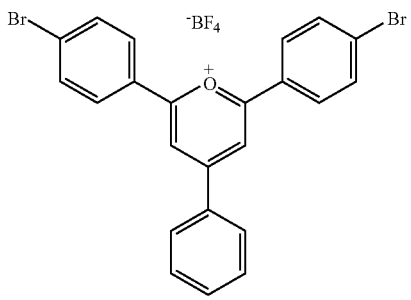

wa6-i2

Triphenylmethanol (6.6 g, 25.4 mmol) was suspended in acetic anhydride (70 mL) and warmed until in solution. Tetrafluoroboric acid (48% in water, 4.15 mL, 31.8 mmol) was slowly added dropwise while cooling the exothermic reaction in a room temperature water bath. Diketone wa6-i1 (10.3 g, 21.2 mmol) was added in portions over a few minutes. Yellow needles of the desired pyrylium salt wa6-i2 began to separate from solution within minutes. The mixture was stirred at room temperature for 16 h, then vacuum filtered and washed with acetic anhydride (3×25 mL) and dried in vacuo at 100° C. to obtain 9.9 g wa6-i2. An additional 540 mg was obtained by treating the filtrate/washings with diethyl ether. Combined yield: 89%.

Example 7

Synthesis of wa6-i3 wa6-i3

Pyrylium salt wa6-i2 (13.85 g, 25.0 mmol) and 4-nitrophenylacetic acid (9.09 g, 50.2 mmol) were slurried in acetic anhydride (26 mL). The mixture was heated to 70 C under a nitrogen atmosphere then triethylamine (7 mL) was added dropwise with stirring. The dark mixture was stored in the refrigerator for 16 h, then filtered and washed with acetic anhydride, then methanol to obtain the desired nitroarene wa6-i3 as a pale yellow powder (7.89 g), which was used without further purification.

Example 8

Synthesis of wa6-i4

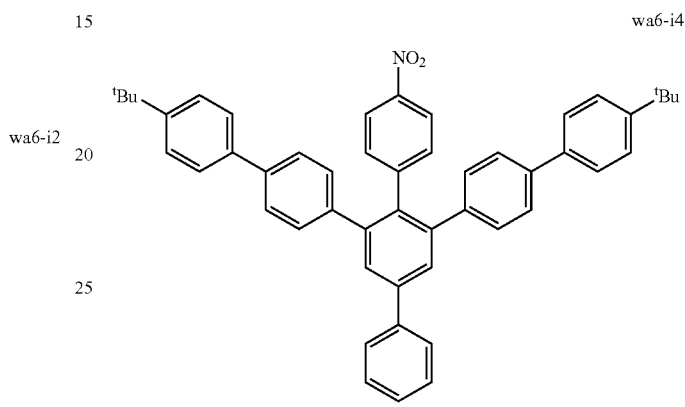

wa6-i4

To a suspension of wa6-i3 (11.81 g, 20.2 mmol) and Pd(PPh$_3$)$_4$ (2.67 g, 2.4 mmol) in toluene (201 ml) was added 4-tert-butylphenylboronic acid (10.77 g, 60.5 mmol) as a solution in EtOH (40 ml). 2 M aqueous Na$_2$CO$_3$ (80 ml) was added and the resulting suspension was heated at 85° C. for 41.5 h, then cooled to 23° C. and extracted with Et$_2$O. The combined organic layers were dried over Na$_2$SO$_4$, filtered and concentrated in vacuo. The residue was dissolved in toluene and filtered through a plug of silica gel and celite then concentrated in vacuo. The residue was suspended in a small amount of CH$_2$Cl$_2$ and filtered, washing with heptane. A second amount of precipitate was collected from the filtrate, again washing with heptane. The filtrate was filtered a third time to afford a gray solid, which was adsorbed onto silica gel and eluted through a short plug of silica and celite with CH$_2$Cl$_2$. The filtrate was combined with the solids obtained previously to afford wa6-i4 (6.14g, 44%), which was used without further purification.

Example 9

Synthesis of wa6-i5

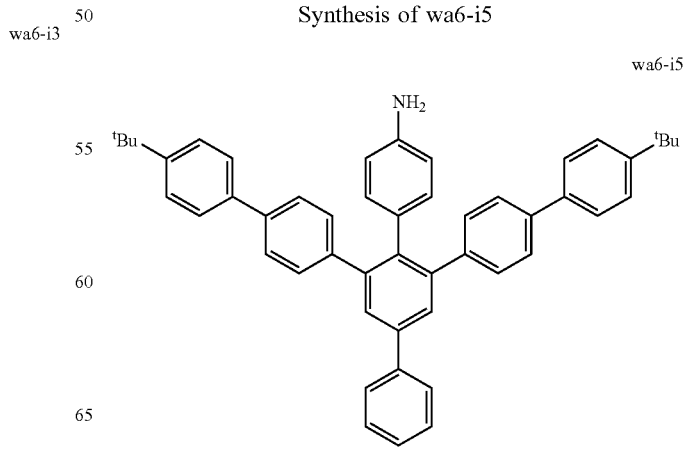

wa6-i5

A suspension of wa6-i4 (9.14 g, 13.2 mmol) and 5% Pd/C (1.84 g) in a mixture of toluene (149 ml) and MeOH (25 ml) was stirred under a balloon of $H_2$ at 55° C. for 17 h. The reaction was cooled to rt, and filtered through a plug of celite, rinsing with toluene. The filtrate was concentrated in vacuo to afford wa6-i5 (8.72 g, 100%), which was used without further purification.

Example 10

Synthesis of wa6-i6

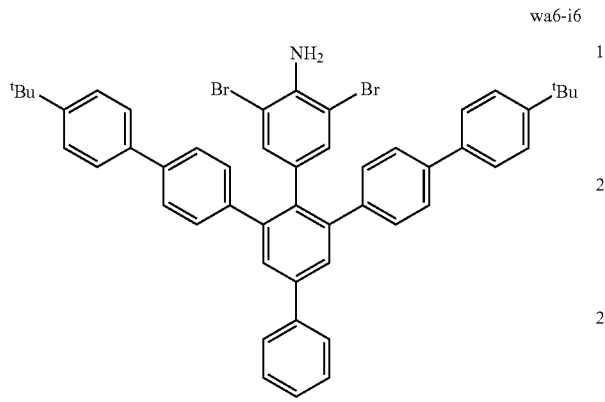
wa6-i6

To an ice cold suspension of wa6-i5 (8.72 g, 13.2 mmol) in acetic acid (102 ml) and $CH_2Cl_2$ (20 ml) was added NaOAc (2.18 g) in portions. Following the completion of the addition, bromine (1.37 ml) was added via syringe. The ice bath was removed, and the reaction stirred at 23° C. under Ar for 1.5 h then poured over ice, resulting in the formation of a yellow solid (7.96 g), which was collected by vacuum filtration. The filtrate was extracted with $CH_2Cl_2$. The organic layer was dried over $Na_2SO_4$, filtered and concentrated in vacuo. The residue was combined with the solid collected previously to afford wa6-i6 (10.13 g, 94%), which was used without further purification.

Example 11

Synthesis of wa6-i7

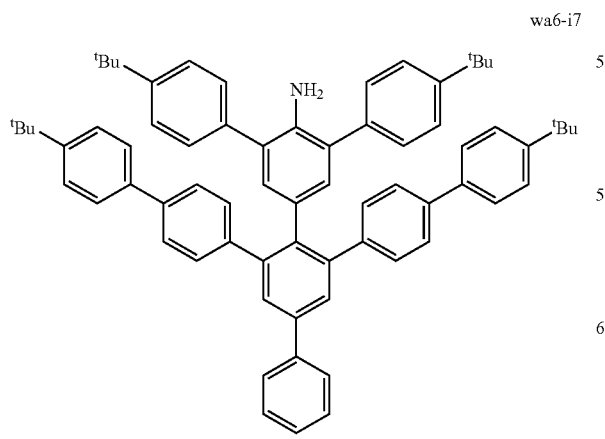
wa6-i7

To a suspension of wa6-i6 (4.5 g, 5.5 mmol) and $Pd(Ph_3P)_4$ (0.722 g, 0.65 mmol) in toluene (54.6 ml) was added 4-tert-butylphenylboronic acid (2.91 g, 16.4 mmol) and EtOH (10.9 ml). The resulting suspension was treated with 2 M aqueous $Na_2CO_3$ (21.7 ml) then heated to 85° C. for 22.5 h. The reaction was cooled to rt, and extracted with toluene. The organic layer was washed with water, dried over $Na_2SO_4$, filtered and concentrated in vacuo. The residue was divided into two portions and purified by flash chromatography ($SiO_2$, 5–50% $CH_2Cl_2$/heptane) on two columns to afford wa6-i7 (1.9 g and 2.16 g, total 4.06 g, 80%).

Example 12

Synthesis of wa6-i8

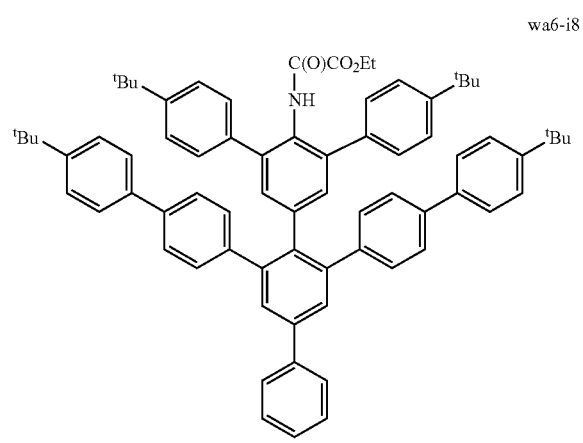
wa6-i8

To a suspension of wa6-i7 (250 mg, 0.27 mmol) in $CH_2Cl_2$ (1.5 ml) was added ethyl chlorooxoacetate (0.032 ml, 0.28 mmol). The resulting solution was stirred at 23° C. for 1 h, then diluted with $CH_2Cl_2$ and washed with saturated aqueous $NaHCO_3$ and water. The organic layer was concentrated in vacuo to afford wa6-i8 (277 mg), which was used without further purification.

Example 13

Synthesis of wa-i9

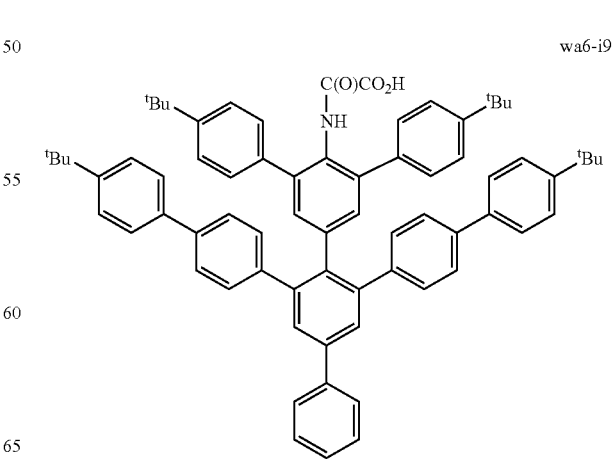
wa6-i9

A suspension of wa6-i8 (246 mg, 0.24 mmol) in iPrOH (1.7 ml) was treated with 2 M NaOH (1.08 ml). The resulting suspension was heated to 60° C. for 1 h, then cooled to 23° C. and acidified with 2 M HCl (pH=2). The solid that formed was filtered, washed with $H_2O$ and dried in vacuo to afford wa6-i9 (220 mg, 92%), which was used without further purification.

Example 14

Synthesis of wa6-i10

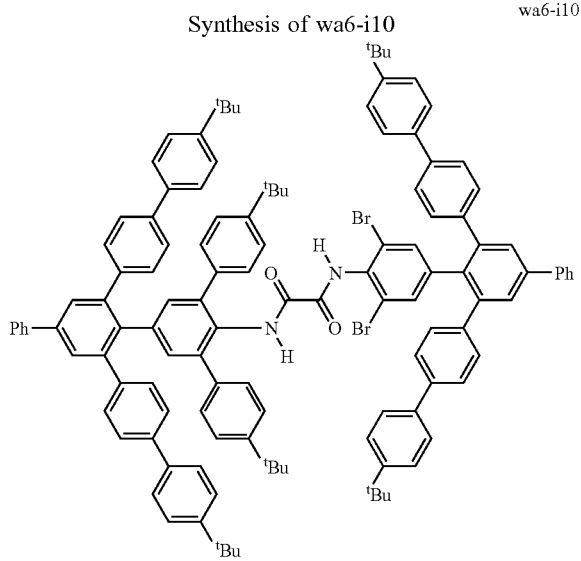

wa6-i10

Amide/acid wa6-i9 (215 mg, 0.215 mmol) was added portionwise to a suspension of NaH (60% in oil, 10 mg, 0.254 mmol) in toluene (2 ml). The resulting suspension was stirred at 23° C. for 15 min then treated with oxalyl chloride (338 μl, 3.88 mmol) and stirred at 23° C. for an additional 15 min. The mixture was concentrated in vacuo, and the residue was treated with wa6-i6 (184 mg, 0.225 mmol) followed by $CH_2Cl_2$ (2 ml). The resulting suspension was stirred at 23° C. for 3 days then concentrated in vacuo to afford crude wa6-i10 (415 mg), which was used without further purification.

Example 15

Synthesis of wa6-i11

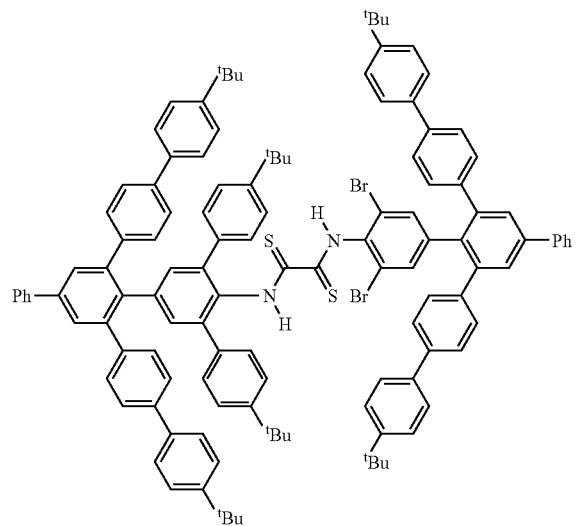

wa6-i11

A suspension of wa6-i10 (385 mg (assume 100% yield from example 10), 0.214 mmol) in o-xylene (1.5 ml) was treated with $P_4S_{10}$ (48 mg, 0.108 mmol). The resulting suspension was heated to 140° C. under Ar for 1.5 h, then cooled to rt. The residue was diluted with toluene and washed with water. The organic layer was dried over $Na_2SO_4$, filtered and concentrated in vacuo to afford wa6-i11 (413 mg), contaminated with residual xylene. The crude product was not purified further.

Example 16

Synthesis of wa6

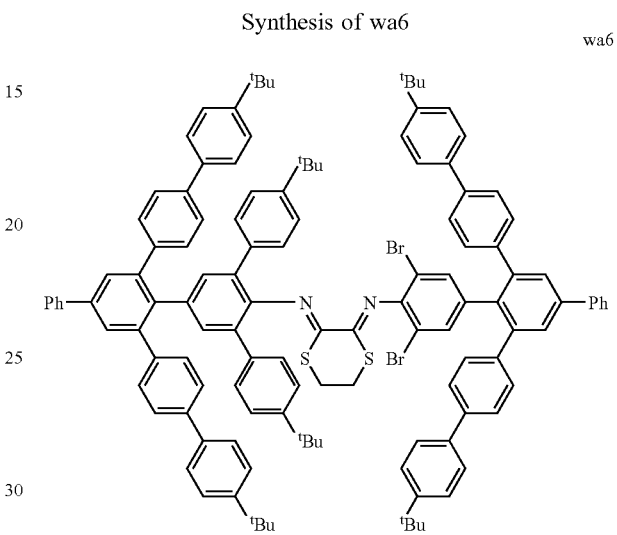

wa6

To a suspension of wa6-i11 (392 mg (assume 100% yield from example 11), 0.214 mmol,) in 1,2-dibromoethane (2.17 ml) was added 2 M NaOH (2.55 ml) and tetrabutylammonium bromide (12.8 mg, 0.04 mmol). The resulting biphasic mixture was stirred rapidly under Ar at 23° C. for 17 h, then diluted with $CH_2Cl_2$ and washed with $H_2O$. The organic layer was dried over $Na_2SO_4$, filtered and concentrated in vacuo. The residue was purified by flash chromatography ($SiO_2$, 20–70% $CH_2Cl_2$/heptane) to afford wa6 (280 mg, 70% from wa6–19).

Example 17

Synthesis of wa5-i1

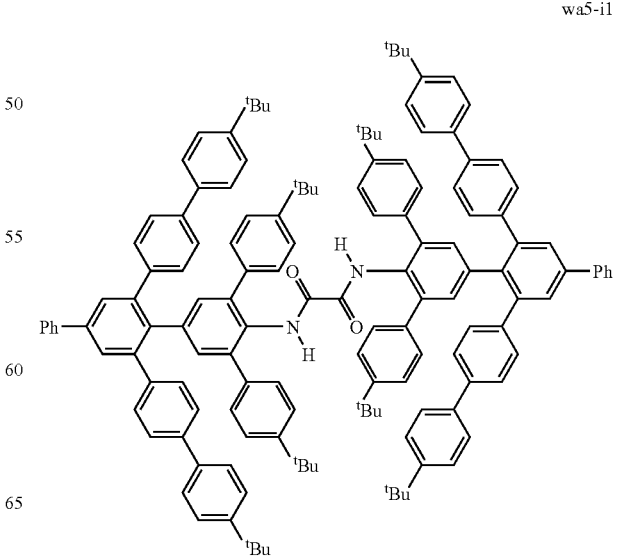

wa5-i1

A solution of wa6-i7 (329 mg, 0.355 mmol) in CH$_2$Cl$_2$ (2 ml) was treated with oxalyl chloride (20 μl, 0.22 mmol). The resulting solution was stirred at 23° C. under Ar for 1 h, then poured into MeOH. The precipitate was filtered and dried in vacuo. NMR indicated the crude product contained a significant amount of wa6-i7, so the mixture was redissolved in CH$_2$Cl$_2$ (2 ml) and treated with oxalyl chloride (10 μl, 0.11 mmol). The resulting mixture was stirred at 23° C. under Ar for 25.5 h, then poured into MeOH. The precipitate was filtered and dried in vacuo to afford wa5-i1 (319 mg), which was used without further purification.

Example 18

Synthesis of wa5-i2

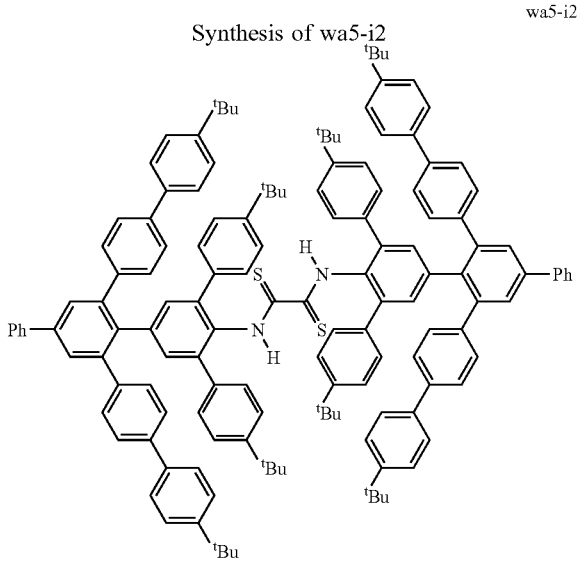

wa5-i2

P$_4$S$_{10}$ (37.5 mg, 0.084 mmol) was added to a suspension of wa5-i1 (319 mg, 0.167 mmol) in o-xylene (1.4 ml). The resulting suspension was heated to 140° C. under Ar for 5.5 h, then cooled to 23° C. overnight. TLC indicated the reaction was not complete, so the mixture was heated to 140° C. for an additional 6 h. The reaction was cooled to 23° C. and allowed to stand under Ar overnight. The suspension was diluted with toluene and washed with H$_2$O. The organic layer was dired over Na$_2$SO$_4$, filtered and concentrated in vacuo to afford wa5-i2 (242 mg), which was used without further purification.

Example 19

Synthesis of wa5

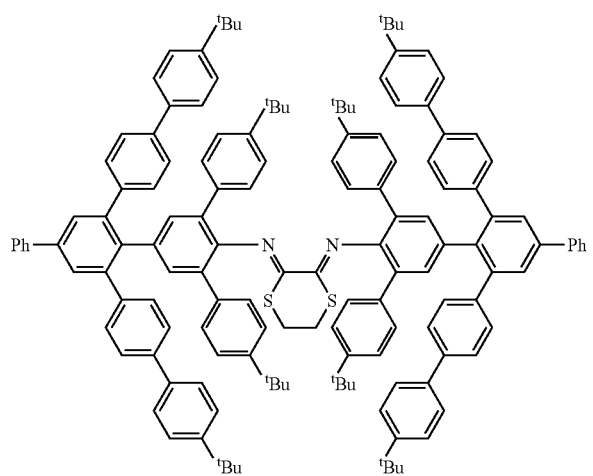

wa5

A suspension of wa5-i2 (242 mg, 0.124 mmol) in 1,2-dibromoethane (1.28 ml) was treated with 2 M NaOH (1.5 ml) and tetrabutylammonium bromide (8mg, 0.025 mmol). The resulting biphasic solution was stirred vigorously under Ar for 4 h, then diluted with CH$_2$Cl$_2$ and washed with H$_2$O. The organic layer was dried over Na$_2$SO$_4$, filtered and concentrated in vacuo. The residue was purified by flash chromatography (SiO$_2$, 15–50% CH$_2$Cl$_2$/heptane) to afford wa5, contaminated with a small amount of an unidentified impurity. The impurity was removed by washing with MeOH to afford wa5 (87.3 mg, 25% from wa6-i7).

Example 20

Ethylene Polymerization with the Nickel Catalyst Derived from Ni(acac)$_7$, Ph$_3$C(C$_6$F$_5$)$_4$ and Ligand v22

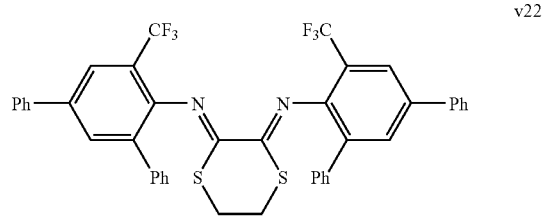

v22

A 1 L Parr® autoclave, Model 4520, was dried by heating under vacuum to 180 C at 0.6 torr for 1 h, then cooled and refilled with dry nitrogen. The autoclave was charged with dry, deoxygenated hexane (450 mL) and 2.0 mL of a 0.25 M solution of triisobutylaluminum in hexanes. The reactor was sealed and heated to 80° C. under nitrogen, then sufficient hydrogen was added to raise the pressure by 8.9 psi, after which ethylene was introduced to raise the total pressure to 250 psig. A sample loop injector was first purged with 2.0 mL dry, deoxygenated dichloromethane (injected into the reactor), and then used to inject 3×2.0 mL of a stock solution (corresponding to a total of 3.0 μmol of pro-catalyst) prepared from 17.34 mL of CH$_2$Cl$_2$ and 2.66 mL of a second stock solution prepared from 45.3 mg ligand v22, 15.0 mg Ni(acac)$_2$, 54 mg Ph$_3$C(C$_6$F$_5$)$_4$ and 19.546 g (14.75 mL) CH$_2$Cl$_2$, followed by 2.0 mL of CH$_2$Cl$_2$, using ethylene gas to force the liquids into the autoclave and raise the pressure to ca. 440 psig, after which time the reactor was isolated and the pressure was allowed to fall to about 380 psig. More ethylene was then reintroduced to raise the pressure back to ca. 430 psig, after which the pressure was allowed to fall to ca. 400 psig, to give an average pressure of 402 psig, and an average temperature was 80.4° C. After 47 min, the reaction was quenched by injection of MeOH, then the reactor was cooled, depressurized and opened. The polyethylene was recovered by concentrating the mixture to dryness under vacuum to obtain 13.01 g amorphous polyethylene, corresponding to 1.55×10$^5$ mol ethylene/mol Ni.

Example 21

Ethylene Polymerization with the Nickel Catalyst Derived from $Ni(acac)_2$, $Ph_3C(C_6F_5)_4$ and Ligand v22

The procedure of Example 20 was followed, except the average temperature was 60.1 C, the average pressure was 605 psig, the partial pressure of hydrogen was 4.49 psi, and the total reaction time was 59.7 min. This afforded 38.6 g amorphous polyethylene, corresponding to $4.6 \times 10^5$ mol ethylene/mol nickel.

Example 22

Ethylene Polymerization with the Nickel Catalyst Derived from $Ni(acac)_2$, $Ph_3C(C_6F_5)_4$ and Ligand v5

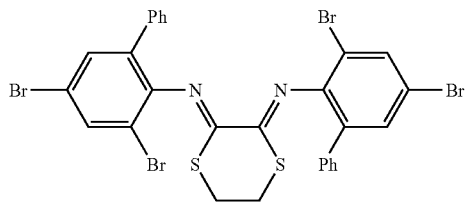

v5

The procedure of Example 20 was followed using 2 μmol of the nickel catalyst derived from $Ni(acac)_2$, $Ph_3C(C_6F_5)_4$ and ligand v5, and an average temperature of 60.8 C, an average pressure of 397 psig, a partial pressure of hydrogen of 5.12 psi, and a total reaction time of 21.7 min. This afforded 38. g partially crystalline polyethylene, corresponding to $6.8 \times 10^5$ mol ethylene/mol nickel.

Example 23

Ethylene Polymerization with the Nickel Catalyst Derived from $Ni(acac)_2$, $Ph_3C(C_6F_5)_4$ and 2,3-bis(2,6-diisopropylphenylimino)butane The procedure of Example 20 was followed using 4.2 μmol of the nickel catalyst derived from $Ni(acac)_2$, $Ph_3C(C_6F_5)_4$ and 2,3-bis(2,6-diisopropylphenylimino)-butane, and an average temperature of 60.5 C, an average pressure of 398 psig, a partial pressure of hydrogen of 4.64 psi, and a total reaction time of 60 min. This afforded 18.7 g polyethylene, corresponding to $1.6 \times 10^5$ mol ethylene/mol nickel.

Example 24

Ethylene Polymerization with the Nickel Catalyst Derived from $Ni(acac)_2$, $Ph_3C(C_6F_5)_4$ and Ligand v4

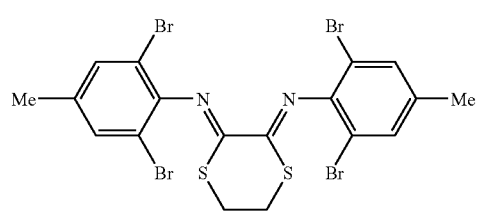

v4

The procedure of Example 20 was followed using 2 μmol of the nickel catalyst derived from $Ni(acac)_2$, $Ph_3C(C_6F_5)_4$ and ligand v4, an initial temperature of 60° C. (the reaction exothermed to 81° C.), an average temperature of 63.7 C, an average pressure of 590 psig, a partial pressure of hydrogen of 4.03 psi, and a total reaction time of 34.5 min. This afforded 33.7 g partially crystalline polyethylene, corresponding to $6.0 \times 10^5$ mol ethylene/mol nickel.

Example 25

Ethylene Polymerization with the Nickel Catalyst Derived from $Ni(acac)_2$, $Ph_3C(C_6F_5)_4$ and Ligand v5

The procedure of Example 22 was repeated using 3 μmol nickel catalyst, 13.32 psi hydrogen, an average temperature of 80.4 C, and an average pressure of 406 psig to obtain 19.9 g polyethylene, corresponding to $2.4 \times 10^5$ mol ethylene/mol Ni.

Ligand syntheses and metal complex syntheses not given above followed procedures similar to those given above or previously described in the cross-referenced applications.

We claim:

1. A catalyst for olefin polymerization, comprising a Group 3–11 metal complex of a bidentate, tridentate, or tetradentate ligand, wherein said complex comprises at least one N-donor fragment of formula 1a or 2b;

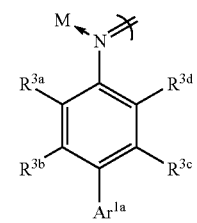

1a

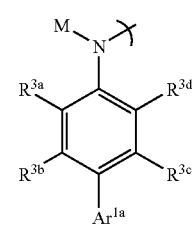

1b wherein:

M is a Group 3–11 transition metal;

$R^{3a-d}$ are each, independently, H, F, Cl, Br, hydrocarbyl, substituted hydrocarbyl, fluoroalkyl, nitro, heteroatom connected hydrocarbyl or heteroatom connected substituted hydrocarbyl; and $Ar^{1a}$ is an aryl or heteroaryl group substituted at one or both ortho positions by a group $Q^2$; wherein $Q^2$ is hydrocarbyl, substituted hydrocarbyl, heteroatom connected hydrocarbyl or heteroatom connected substituted hydrocarbyl.

2. The catalyst according to claim 1 wherein M is a Group 8–10 metal.

3. The catalyst according to claim 2, wherein M is nickel, and $Q^2$ is sufficiently long to extend sufficiently close to the metal M to increase the catalyst productivity at elevated temperatures, or in the presence of hydrogen, or both, relative to an otherwise similar catalyst wherein $Q^2$ is replaced by H, Me, or Ph.

4. The catalyst according to claim 2, wherein M is nickel, and $Q^2$ is sufficiently long to extend sufficiently close to the metal M to increase the regioselectivity or stereoselectivity of comonomer incorporation, relative to an otherwise similar catalyst wherein $Q^2$ is replaced by H, Me, or Ph.

5. The catalyst according to claim 2, wherein M is nickel, and $Q^2$ is sufficiently long to extend sufficiently close to the metal M to decrease the amount of chain-running, relative to an otherwise similar catalyst wherein $Q^2$ is replaced by H, Me, or Ph.

6. The catalyst according to claim 2, wherein M is palladium, and $Q^2$ is sufficiently long to extend sufficiently close to the metal M to decrease the amount of chain-running, relative to an otherwise similar catalyst wherein $Q^2$ is replaced by H, Me, or Ph.

7. The catalyst according to claim 2, wherein M is nickel, and $Q^2$ is sufficiently long to extend sufficiently close to the metal M to increase the chain-running stereoselectivity, relative to an otherwise similar catalyst wherein $Q^2$ is replaced by H, Me, or Ph.

8. The catalyst according to claim 2, wherein M is nickel, and $Q^2$ is sufficiently long to extend sufficiently close to the metal M to decrease the rate of activation of the catalyst when an alkylaluminum reagent is used as cocatalyst, relative to an otherwise similar catalyst wherein $Q^2$ is replaced by H, Me, or Ph.

9. The catalyst according to claim 2 which comprises a bidentate ligand selected from Set 1;

Set 1

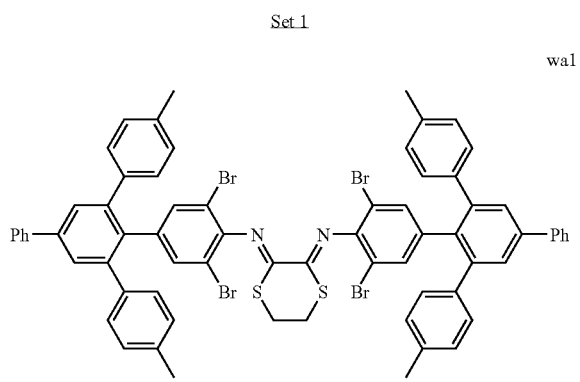

wa1

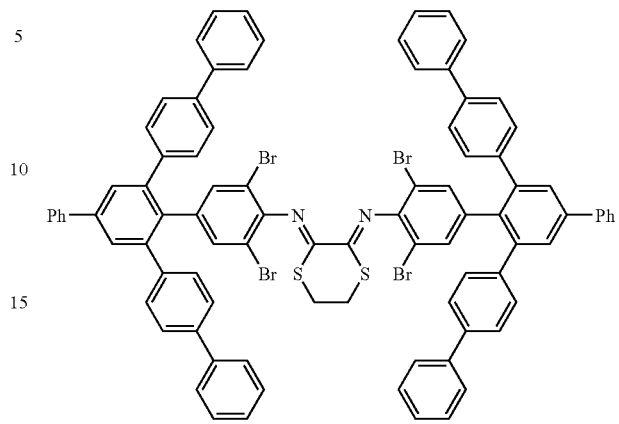

wa2

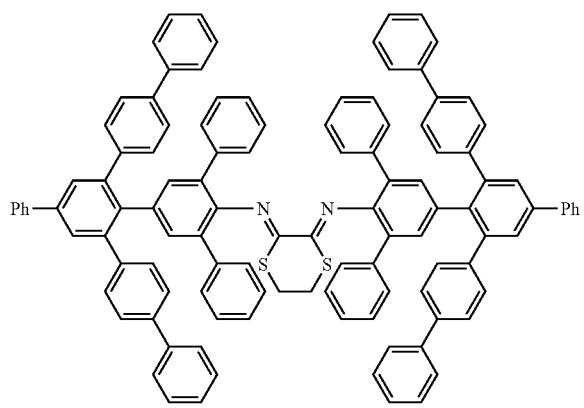

wa3

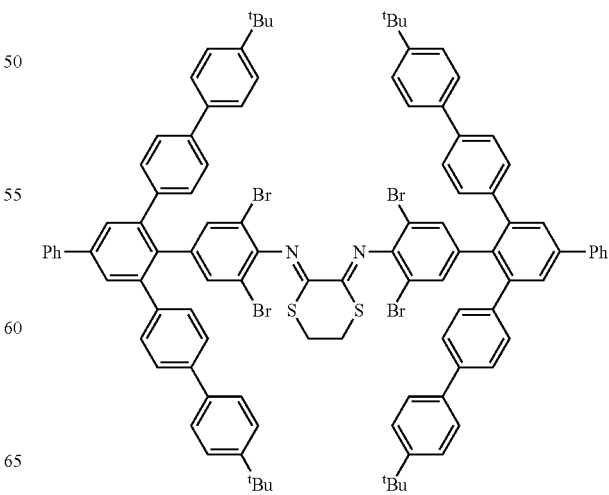

wa4

-continued
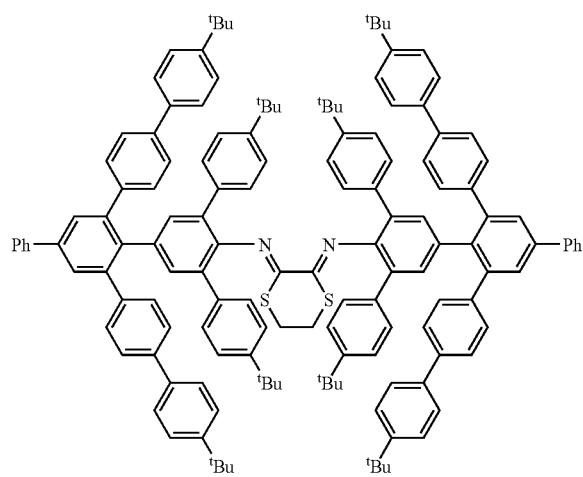
wa5
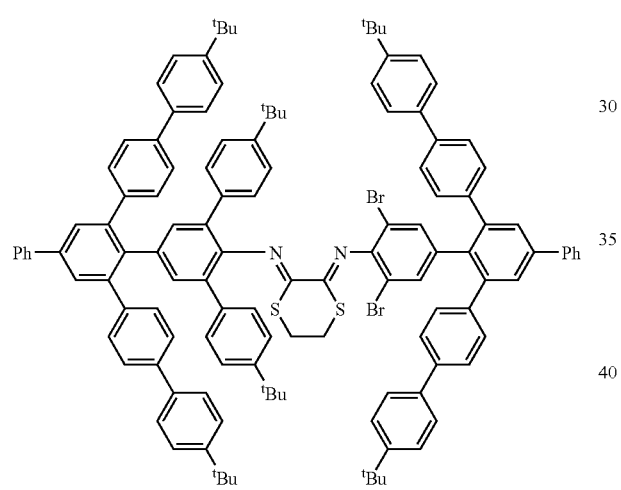
wa6
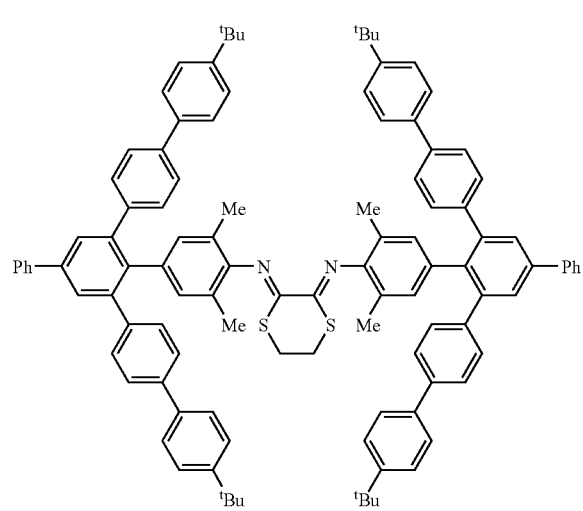
wa7
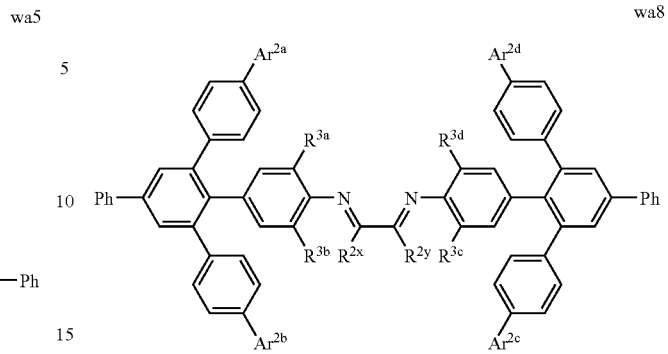
wa8
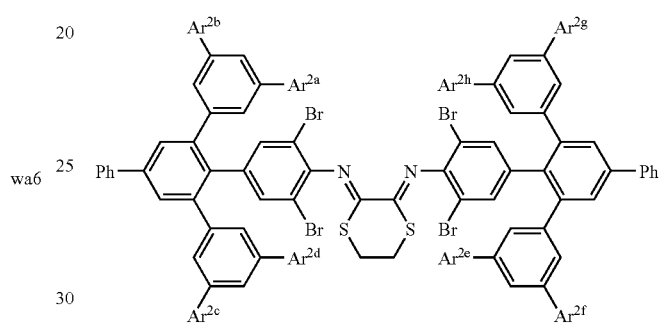
wa9
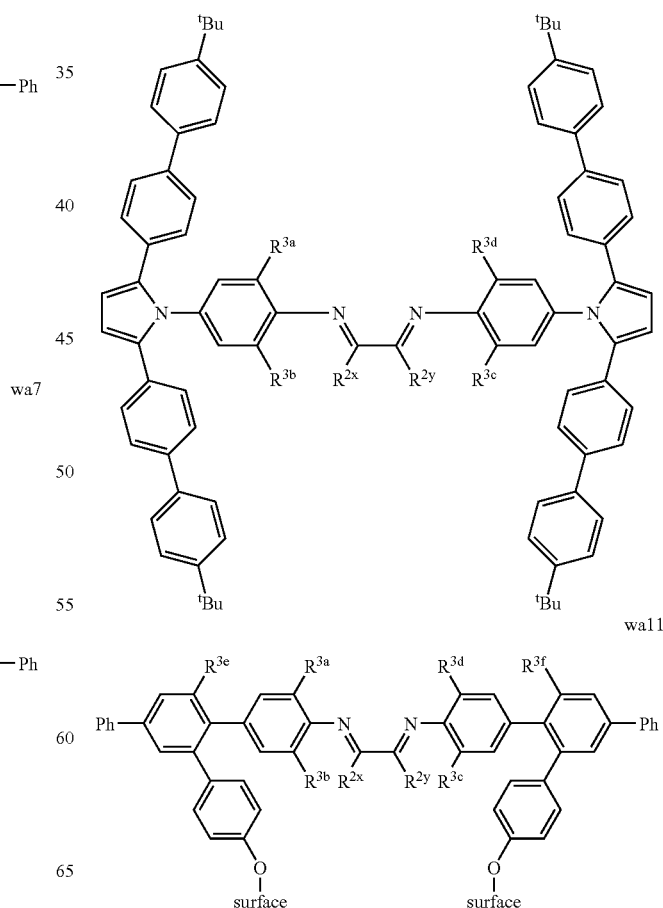
wa10
wa11

-continued
wa12
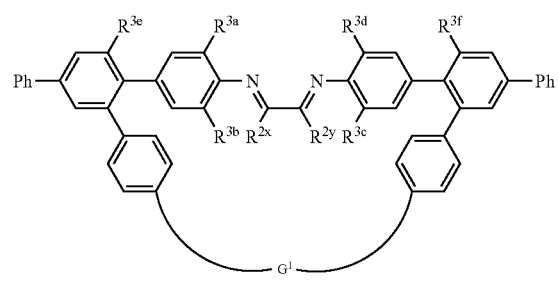
wa13
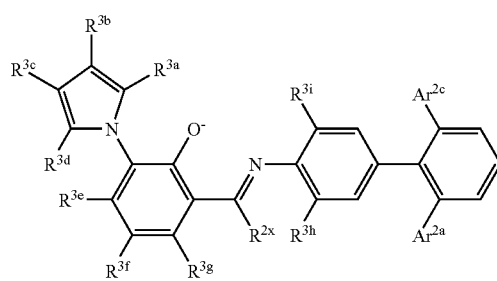
wa14
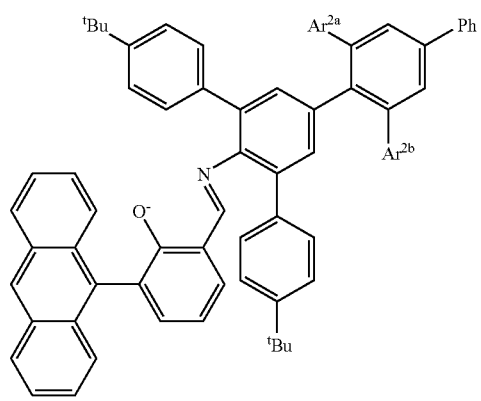
wa15
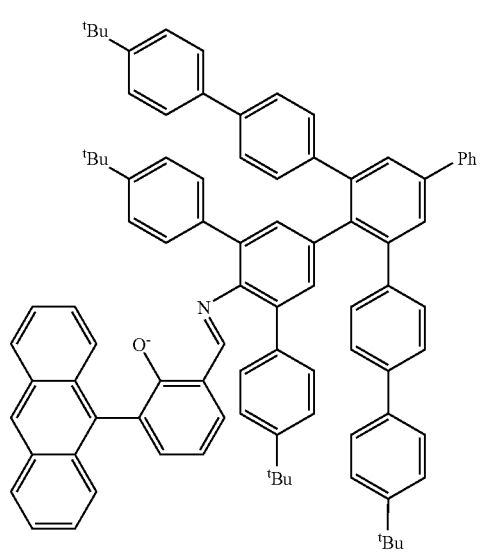
-continued
wa16
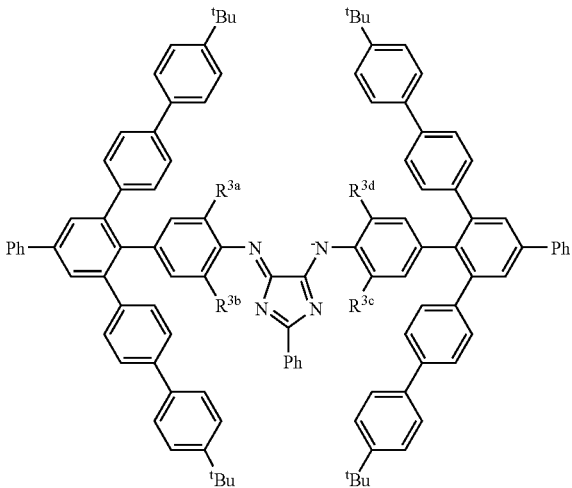
wa17
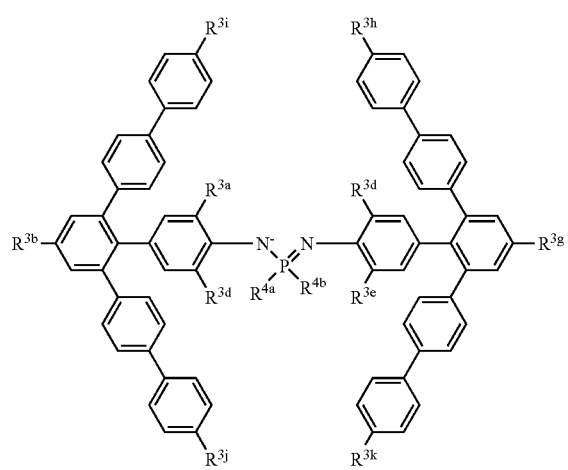
wa18
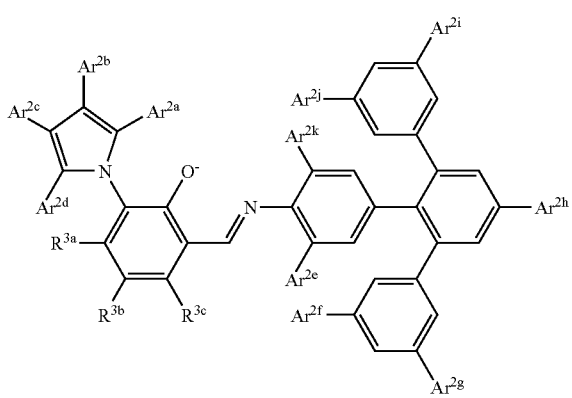

-continued shcr6

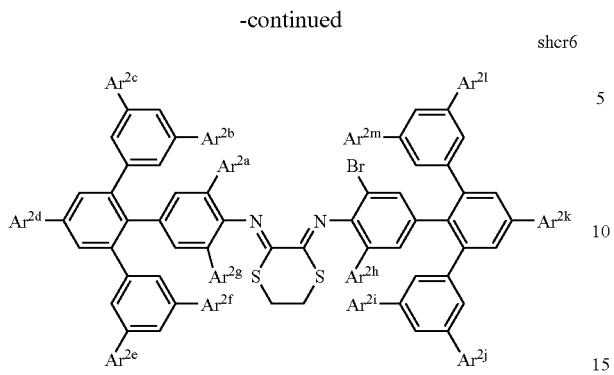

-continued tri2

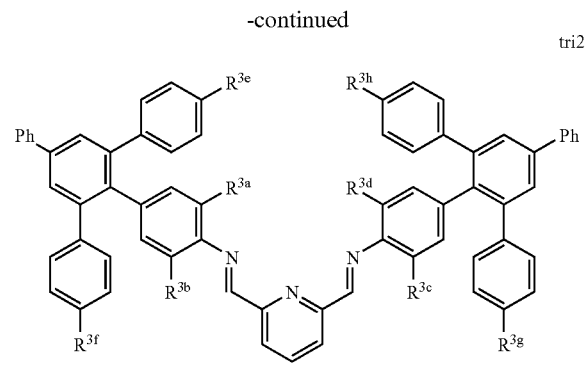

wherein:
- $R^{2x,Y}$ are each independently H, hydrocarbyl, substituted hydrocarbyl, heteroatom connected hydrocarbyl, heteroatom connected substituted hydrocarbyl; silyl, or ferrocenyl; in addition, $R^{2x}$ and $R^{2y}$ may be linked by a bridging group;
- $R^{3a-k}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro;
- $R^{4a,b}$ are each independently hydrocarbyl, substituted hydrocarbyl, heteroatom connected hydrocarbyl, heteroatom connected substituted hydrocarbyl; in addition, $R^{4a}$ and $R^{4b}$ may be linked by a bridging group;
- "surface" refers to a silicon or other atom which is part of, or attached to, a solid support;
- $G^1$ is a divalent bridging group; and
- $Ar^{2a-m}$ are each independently hydrocarbyl, substituted hydrocarbyl, heteroatom attached hydrocarbyl, heteroatom attached substituted hydrocarbyl, halo, nitro, boryl, or trialkoxysilane.

10. The catalyst according to claim 2, wherein M is iron or cobalt, the catalyst comprises a tridentate ligand, and $Q^2$ which is sufficiently long to extend sufficiently close to the metal M to increase the catalyst productivity at elevated temperatures.

11. The catalyst according to claim 10, wherein said tridentate ligand is selected from Set 2;

Set 2 wherein:
- $R^{2x,y}$ are each independently H, hydrocarbyl, substituted hydrocarbyl, heteroatom connected hydrocarbyl, heteroatom connected substituted hydrocarbyl; silyl, or ferrocenyl; and
- $R^{3a-k}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro.

12. The catalyst according to claim 1, comprising a titanium or zirconium complex of a bidentate ligand selected from Set 3;

Set 3 da1

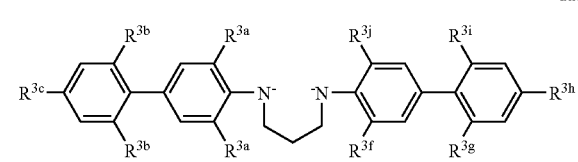

ma1

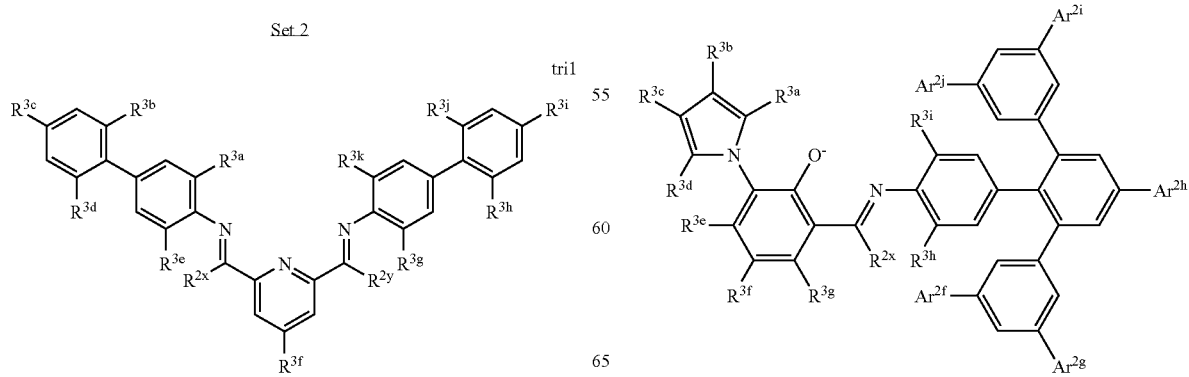

tri1

-continued

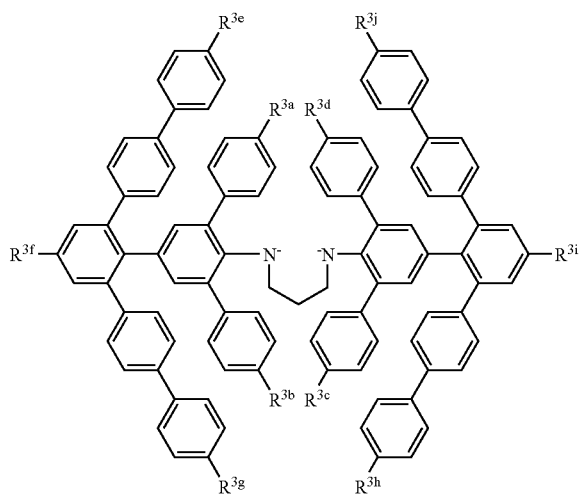
da2 wherein:
R$^{2X}$ is H, hydrocarbyl, substituted hydrocarbyl, heteroatom connected hydrocarbyl, heteroatom connected substituted hydrocarbyl; silyl, or ferrocenyl;
R$^{3a-j}$ are each independently H, hydrocarbyl, substituted hydrocarbyl, heteroatom connected hydrocarbyl, heteroatom connected substituted hydrocarbyl, fluoroalkyl, fluoro, chloro, or bromo; and
Ar$^{2a-j}$ are each independently hydrocarbyl, substituted hydrocarbyl, heteroatom attached hydrocarbyl, heteroatom attached substituted hydrocarbyl, halo, nitro, boryl, or trialkoxysilane.

13. The catalyst according to claim 1, further comprising a solid support.

14. The catalyst according to claim 13, which is attached to the solid support via a covalent bond to the group Ar$^{1a}$.

15. A process for the polymerization of olefins, comprising contacting one or more olefins with the catalyst of claim 1.

16. The process according to claim 15, wherein at least one of said olefins is ethylene.

17. The process according to claim 15, wherein the olefin is ethylene, M is nickel, the temperature is at least 80° C., the pressure is less than about 800 psig, sufficient hydrogen is added to reduce the number average molecular weight of the polymer by at least 20% relative to an otherwise similar reaction conducted in the absence of hydrogen, the catalyst productivity is at least 500 kg polyethylene per g nickel, and the polymer has a DSC first cycle peak melting point greater than 131° C.

18. The process according to claim 17, wherein sufficient hydrogen is added to reduce the number average molecular weight of the polymer by at least 50% relative to an otherwise similar reaction conducted in the absence of hydrogen, and the polymer has a DSC first cycle peak melting point greater than 133° C.

19. The process according to claim 15, wherein at least one of the olefins is ethylene, M is palladium and the amount of chain running is reduced.

20. A catalyst for the polymerization of olefins, comprising a nickel complex of a ligand of formula 2a;

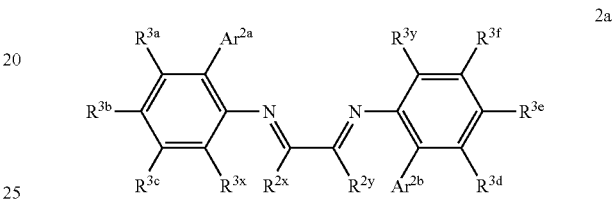
2a wherein:
R$^{2x,y}$ are each independently hydrocarbyl, substituted hydrocarbyl, heteroatom connected hydrocarbyl, heteroatom connected substituted hydrocarbyl, or silyl; in addition, R$^{2x}$ and R$^{2y}$ may be linked by a bridging group;
R$^{3a-f}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, iodo, cyano, or nitro;
R$^{3x,y}$ are each independently halo or fluoroalkyl; and
Ar$^{2a,b}$ are each independently aryl or heteroaryl.

21. The catalyst according to claim 20, wherein R$^{2x}$ and R$^{2y}$ are linked by a bridging group.

22. A process for the polymerization of olefins comprising contacting ethylene and optionally other olefins with the catalyst of claim 20 in the presence of sufficient hydrogen to reduce the number average molecular weight of the polymer by at least 10% relative to an otherwise similar process carried out in the absence of hydrogen.

* * * * *